US011400149B2

(12) United States Patent
Yao et al.

(10) Patent No.: US 11,400,149 B2
(45) Date of Patent: Aug. 2, 2022

(54) EBOLA VIRUS AND MARBURG VIRUS GLYCOPROTEIN MUCIN-LIKE DOMAIN REPLACEMENT EXPRESSION SYSTEM USED AS NEW VACCINE APPROACHES

(71) Applicant: UNIVERSITY OF MANITOBA, Winnipeg (CA)

(72) Inventors: Xiaojian Yao, Winnipeg (CA); Zhujun Ao, Winnipeg (CA); Gary Kobinger, Winnipeg (CA)

(73) Assignee: University of Manitoba, Winnipeg (CA)

( * ) Notice: Subject to any disclaimer, the term of this patent is extended or adjusted under 35 U.S.C. 154(b) by 120 days.

(21) Appl. No.: 16/772,348

(22) PCT Filed: Dec. 11, 2018

(86) PCT No.: PCT/CA2018/051577
§ 371 (c)(1),
(2) Date: Jun. 12, 2020

(87) PCT Pub. No.: WO2019/113688
PCT Pub. Date: Jun. 20, 2019

(65) Prior Publication Data
US 2021/0069316 A1 Mar. 11, 2021

Related U.S. Application Data

(60) Provisional application No. 62/598,131, filed on Dec. 13, 2017.

(51) Int. Cl.
| | |
|---|---|
| *A61K 39/12* | (2006.01) |
| *A61K 39/00* | (2006.01) |
| *C12N 7/00* | (2006.01) |
| *C07K 14/005* | (2006.01) |
| *A61K 39/145* | (2006.01) |
| *A61K 39/385* | (2006.01) |
| *C12N 15/62* | (2006.01) |

(52) U.S. Cl.
CPC ............ *A61K 39/12* (2013.01); *A61K 39/385* (2013.01); *C07K 14/005* (2013.01); *C12N 15/62* (2013.01); *A61K 2039/5258* (2013.01); *A61K 2039/6075* (2013.01); *C12N 2740/16023* (2013.01); *C12N 2740/16034* (2013.01); *C12N 2740/16134* (2013.01); *C12N 2760/14123* (2013.01); *C12N 2760/14134* (2013.01)

(58) Field of Classification Search
CPC ........ C07K 14/005; A61K 39/12; C12N 7/00; A61P 37/04; Y02A 50/30
See application file for complete search history.

(56) References Cited

FOREIGN PATENT DOCUMENTS

WO 2003092582 11/2003

OTHER PUBLICATIONS

Martinez et al., "Impact of Ebola Mucin-like domain on antiglycoprotein antibody responses induced by ebola virus-like particles", The Journal of infectious diseases, 2011, 204:S825-S832.*
Wang et al., "Epitope-focused immunogens against the CD4-binding site of HIV-1 envelope protein induce neutralizing antibodies against auto- and heterologous viruses", The Journal of Biological Chemistry, 2017,293:830-846.*
Martinez et al., "Impact of Ebola Mucin-Like Domain on Antiglycoprotein Antibody Responses Induced by Ebola Virus-Like Particles". The Journal ofInfectious Diseases, 2011, vol. 204, pp. S825-S832, ISSN 0022-1899.
Wang et al., "Epitope focused immunogens against the CD4-binding site of HIV-1 envelope protein induce neutralizing antibodies against auto- and heterologous viruses". The Journal of Biological Chemistry, published on line Nov. 29, 2017 (Nov. 29, 2017), vol. 293, pp. 830-846, ISSN 1083-351X.
Tran et al., "Spatial Localization of the Ebola Virus GlycoproteinMucin-Like Domain Determined by C,yo-Electron Tomography". Journal of Virology, Sep. 2014 (Sep. 2014), vol. 88, No. 18, pp. 10958-10962, ISSN 1098-5514.

* cited by examiner

*Primary Examiner* — Barry A Chestnut
(74) *Attorney, Agent, or Firm* — Michael R Williams; Ryan W Dupuis; Ade & Company Inc.

(57) ABSTRACT

We have developed a series of Ebola vims envelope glycoprotein (EboGP)-based chimeric fusion proteins that are still able to maintain an efficient EboGP-mediated virus entry in various cell types including human antigen-presenting cells (APCs) while presenting large viral polypeptides, such as HIV Env v3-v5 domain (as large as 241 aa), at the apex and the sides of each EboGP monomer to elicit robust host immune responses. This invention demonstrates the feasibility of an EboGP-based chimeric fusion technology as a novel vaccine approach against different microbial pathogens, including that in human and animals, and against cancers.

Figure 5:
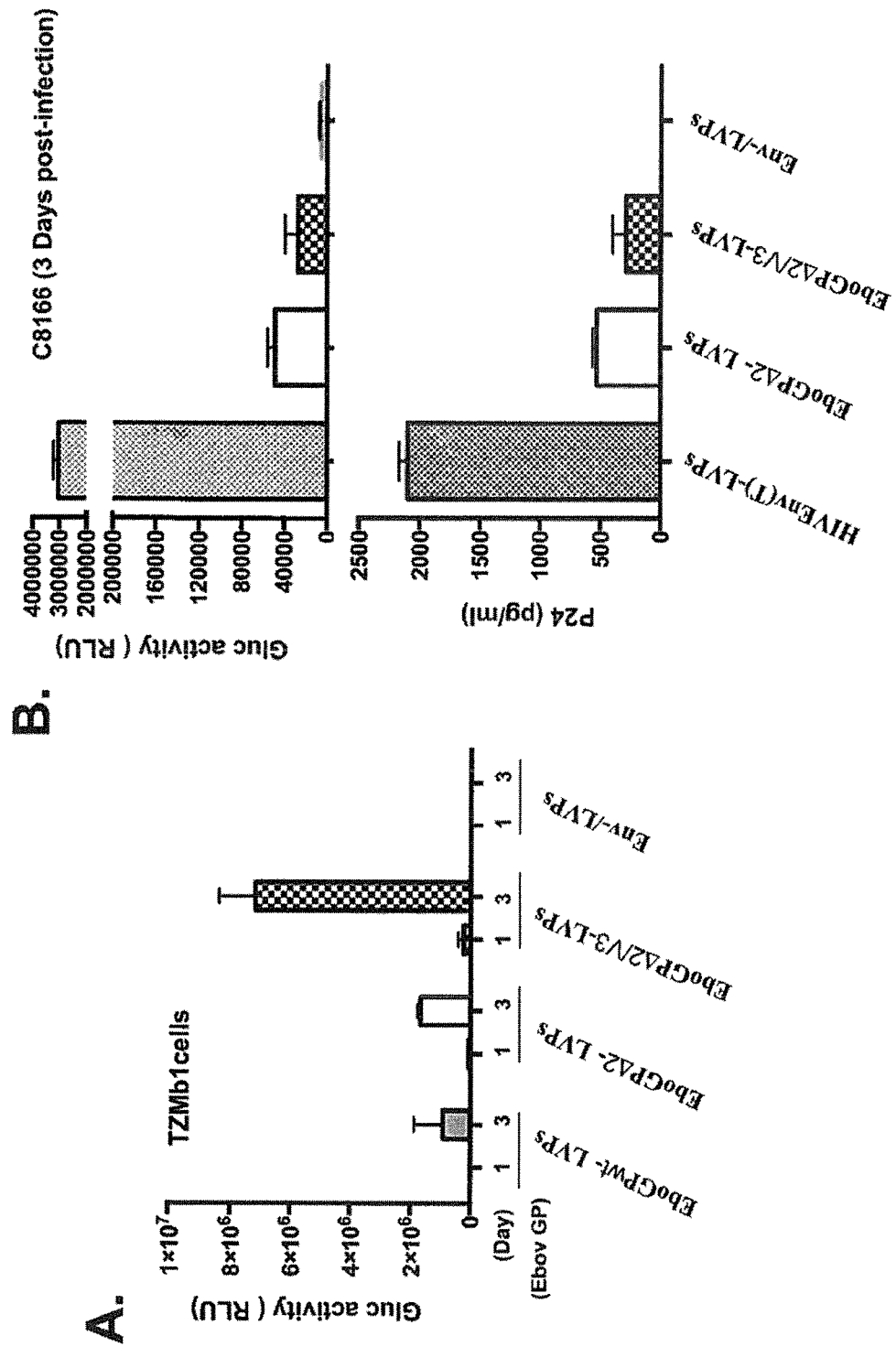

13 Claims, 11 Drawing Sheets
Specification includes a Sequence Listing.

a. rVSVΔG/ENV/VSVG b. rVSVΔG/ENV/EboGP c. rVSVΔG/ENV/EboGPΔM/V3

B. rVSV Immunization

C. Anti-gp120 ELISA

Fig. 11.

EBOLA VIRUS AND MARBURG VIRUS GLYCOPROTEIN MUCIN-LIKE DOMAIN REPLACEMENT EXPRESSION SYSTEM USED AS NEW VACCINE APPROACHES

PRIOR APPLICATION INFORMATION

The instant application is a 371 of PCT CA2018/051577, filed Dec. 11, 2018 and entitled "Ebola Virus Glycoprotein Mucin-Like Domain Replacement Expression System used as New Vaccine Approaches", now abandoned, which claims the benefit of U.S. Provisional Patent Application Ser. No. 62/598,131, filed Dec. 13, 2017, entitled "Ebola Virus Glycoprotein Mucin-Like Domain Replacement Expression System used as New Vaccine Approaches", the contents of which are incorporated herein by reference.

BACKGROUND OF THE INVENTION

Acquired immune deficiency syndrome (AIDS) is a slow degenerative disease of the immune and nervous systems resulting from HIV infection. This infectious disease is the fourth leading cause of human death worldwide and Global estimates of the HIV-1 pandemic indicate that there are an estimated 34 million people living with HIV-1 and 12 million cumulative AIDS related deaths so far (7). The pathogenesis of HIV-1 infection is linked closely to the replication of the virus in vivo (15, 42). The development of anti-HIV chemotherapy was a key success and has had a major impact on the survival of infected individuals. However, chemotherapy can not eliminate the virus from the body and the constant occurrence of drug-resistant HIV variants limits the application of anti-HIV chemotherapy (37, 40). In addition, issues related to cost and/or availability exclude a large portion of the HIV positive population in developing countries indicating that long-term intervention with anti-HIV chemotherapy will not control the global epidemic. Certainly, the development of an efficient protective vaccine to prevent AIDS dissemination has become a priority.

An HIV vaccine (RV144) trial using a prime with a canarypox vector (ALVAC) expressing gag/pol/nef and a boost with a recombinant HIV gp120 showed a modest vaccine efficacy of 31% (35). Interestingly, higher titers of non-neutralizing IgG antibodies against the V1/V2 region of the envelope protein showed greater association with reduced infection in the RV144 trial than cytolytic CD8+ T cell responses while broadly neutralizing antibodies (bNAb) were rarely observed (13), However, the modest success of RV144 does not discount the importance of bNAb in protection considering that administration of bNAbs to macaques have provided the best immune-associated protection from SHIV infection to date (8, 23). These outcomes from in vivo studies provide strong evidence for the promise of the development of new vaccine approaches capable of generating more robust immunity against HIV.

Ebola virus and Marburg virus are among the most virulent and fatal pathogens known to humans. These viruses cause severe hemorrhagic fevers, with case fatality rates of 88%. In March 2014, the largest Ebola outbreak in history exploded across West African and as of February, 2015, the World Health Organization has reported a total of 23,253 Ebola virus disease (EVD) cases and 9,380 deaths. The EVD outbreak has stimulated investigation of several different therapeutic strategies that target specific viral structures and mechanisms of EBOV. Preventing the entry of EBOV into host cells is an attractive strategy and a limited number of compounds, chemical substances and EBOV glycoprotein-specific monoclonal antibodies (MAb) have been found to inhibit EBOV infection by blocking viral entry (5, 11, 33, 41). Some of these therapeutic agents are now entering accelerated human trials in EVD-endemic countries. Furthermore, the anti-EBOV vaccine (a VSV vector expressing EBOV-GP (rVSVΔG/ZEBOVGP) clinic trial showed the safety (1) and efficacy (14, 16, 29) of this vaccine. These findings suggest that Ebo-GP has strong immunogenicity, and the presence of viral glycoprotein in vivo may stimulate robust protective immune responses. This may be because Ebo-GP has a preference for dendritic cells, monocytes and macrophages (25, 26). Additional studies revealed that EBOV-GP can stimulate human dendritic cells through NF-kappaB and MAPK signaling pathways, and enhances innate and adaptive immune responses (4, 27). Dendritic cells (DCs) are specialized cell lineages that form a critical link between the innate and adaptive immune responses (24). After being stimulated or following uptake of antigen, DCs initiate immune responses via the secretion of chemokines and proinflammatory cytokines and the up-regulation of a variety of costimulatory and chemokine receptors. After maturation, they efficiently present antigens and initiate both adaptive immune responses and innate immune responses (9, 12). In addition, DCs can release specific cytokines, toward the activation and guide Th1 and/or Th2 arm(s) of T cell responses to pathogens. Thus, given their central role in the development of immunity, DCs are usually targeted by pathogens that are thought to evade host immune responses. That may also be the reason why when Ebo-GP was used as an immunogen, this protein may elicit robust immune responses.

It is known that the Ebo-GP contains a mucin-like domain (MLD), encompassing residues 305-308 to 501, which is highly glycosylated (FIG. 2) (17, 22, 32). Although it has multiple functions during EBOV infection, including enhancing viral attachment to target cell surfaces (28, 30), protecting conserved regions of GP, including the receptor binding site, from neutralizing antibody recognition (21, 36, 43), and masking immune regulatory molecules, such as major histocompatibility complex1 (MHC1), on infected cell surfaces (36), it is dispensable for EBOV infections in vitro (18, 38) and is not highly conserved (20). Very interestingly, previous studies showed that this mucin-like region is located at the apex and the sides of each glycoprotein monomer (FIG. 1A-D) (39). Also, it has been shown that the removal of this MLD region greatly enhanced EBOVGP-mediated lentiviral vector entry (31), suggesting it is indeed dispensable for the protein's cell entry activity.

Based on this information, we hypothesized that, if we could replace the mucin-like domain (MLD) within the EboGP with a heterologous polypeptide (such as polypeptides from HIV or other pathogens, or cancer specific antigens), the heterologous polypeptides will also be presented at the apex and the sides of each EboGP chimeric fusion protein, and furthermore they will not affect EboGP cell entry ability. In this way, the inserted heterologous polypeptides are able to be presented as antigenic peptides to antigen-presenting cells (APCs) and the immune system. it is feasible that when the combination of antigenicity of the inserted polypeptides (such as polypeptides from HIV) and DC-targeting affinity of EboGP will cause the EboGP-based chimeric fusion protein elicits efficient immune responses against these inserted antigenic polypeptides. In this way, we can develop novel and potent vaccine approaches, including dual action vaccine approaches, against different viral pathogens, especially for anti-HIV and EBOV infections, and even for the development of anticancer vaccines.

SUMMARY OF THE INVENTION

According to an aspect of the invention, there is provided a fusion protein comprising a peptide of interest inserted in the mucin-like domain of Ebola Virus glycoprotein.

In some embodiments, the mucin-like domain comprises amino acids 305-501 of the Ebola Virus glycoprotein.

In some embodiments, the mucin-like domain consists of amino acids 305-501 of the Ebola virus glycoprotein.

In some embodiments, the mucin-like domain is a tolerated deletion of the mucin-like domain.

In some embodiments, the fusion protein further comprises the HIV glycoprotein V3 and/or v3-v5 domain.

In some embodiments, there is provided a nucleic acid encoding the fusion protein described above.

In some embodiments, there is provided a virus-like particle comprising the fusion protein described above.

According to another aspect of the invention, there is provided a method of targeting a peptide of interest to an antigen presenting cell comprising:

providing a virus-like particle comprising as glycoprotein an Ebola Virus glycoprotein fusion protein comprising a protein or peptides of interest inserted in the mucin-like domain of the Ebola Virus glycoprotein; and immunizing an individual in need of immunization against the peptide of interest with an effective amount of the virus-like particle.

According to another aspect of the invention, there is provided a method of eliciting an enhanced immune response against a peptide of interest comprising:

providing a virus-like particle comprising as glycoprotein an Ebola Virus glycoprotein fusion protein comprising a protein or peptides of interest inserted in the mucin-like domain of the Ebola Virus glycoprotein; and immunizing an individual in need of immunization against the peptide of interest with an effective amount of the virus-like particle.

According to another aspect of the invention, there is provided a method of targeting a peptide of interest to an antigen presenting cell comprising:

preparing a fusion protein comprising an Ebola Virus glycoprotein comprising a peptide of interest inserted in the mucin-like domain of the Ebola Virus glycoprotein;

assembling virus-like particles comprising the fusion protein; and immunizing an individual in need of immunization against the peptide of interest with an effective amount of the virus-like particle.

According to another aspect of the invention, there is provided a method of eliciting an enhanced immune response against a peptide of interest comprising:

preparing a fusion protein comprising an Ebola Virus glycoprotein comprising a peptide of interest inserted in the mucin-like domain of the Ebola Virus glycoprotein;

assembling virus-like particles comprising the fusion protein; and immunizing an individual in need of immunization against the peptide of interest with an effective amount of the virus-like particle According to a further aspect of the invention, there is provided a method of targeting a peptide of interest to an antigen presenting cell comprising:

preparing a fusion protein comprising HIV V3 or V3-V5 domain fused to the peptide of interest;

assembling virus-like particles comprising the fusion protein; and immunizing an individual in need of immunization against the peptide of interest with an effective amount of the virus-like particle.

BRIEF DESCRIPTION OF THE DRAWINGS AND TABLES

FIG. 1. Schematic diagram of the three-dimensional structure of the wild type EboGP (A (a top view) and B (a side view)), and compared to a MLD-deleted EboGP (C and D). The MLD is shown at the apex and the side of the glycoprotein. The EboGP-based chimeric fusion proteins EboGP/HIVV3, V3/V5 or ZikaDIII are shown in E and F. The HIVv3 or ZikaDIII are located at the apex and the side of the MLD-deleted EboGP.

Figure 2:
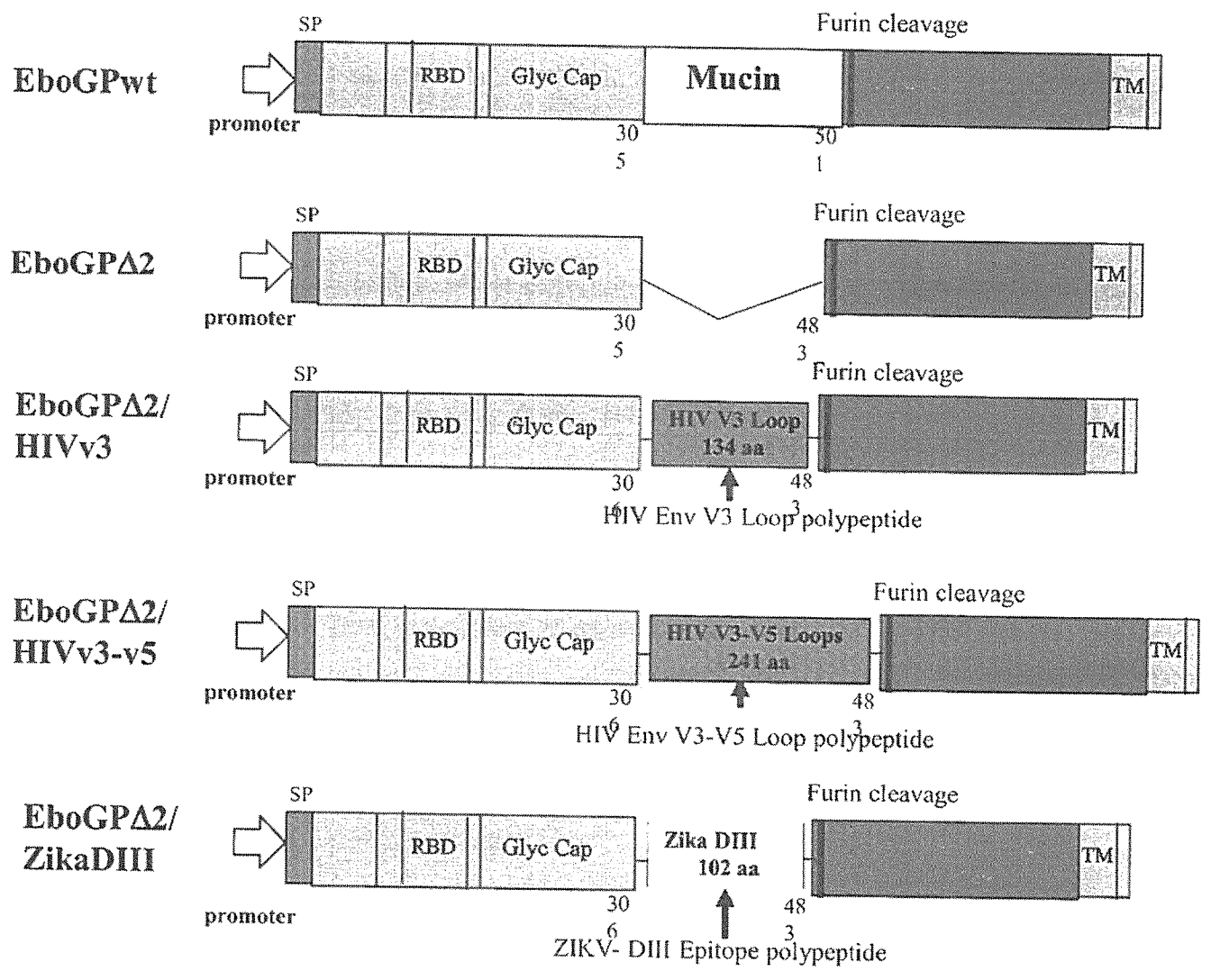

FIG. 2. Construction of EboGP/HIV-V3 and EboGP/ZikaDIII chimeric protein expressors. A codon-optimized EboGP Gene and MLD-deleted (deletion encompassing aa 306 to 483) EboGP gene sequences (the sequences shown in Table 1) were inserted into a mammalian cell expression vector, and named EboGPwt and EboGPΔ2, respectively. To further construct different EboGP chimeric protein expressors, PCR amplified gene sequences (termed as HIVv3, and v3-v5 or ZikaDIII domain sequence, which are shown in Table 2) were inserted into MLD-deleted EboGP gene, and cloned into the mammalian cell expression vector, designated as EboGPΔ2/HIV-v3, EboGPΔ2/HIVv3-v5, or EboGPΔ2/ZikaDIII.

Figure 3:
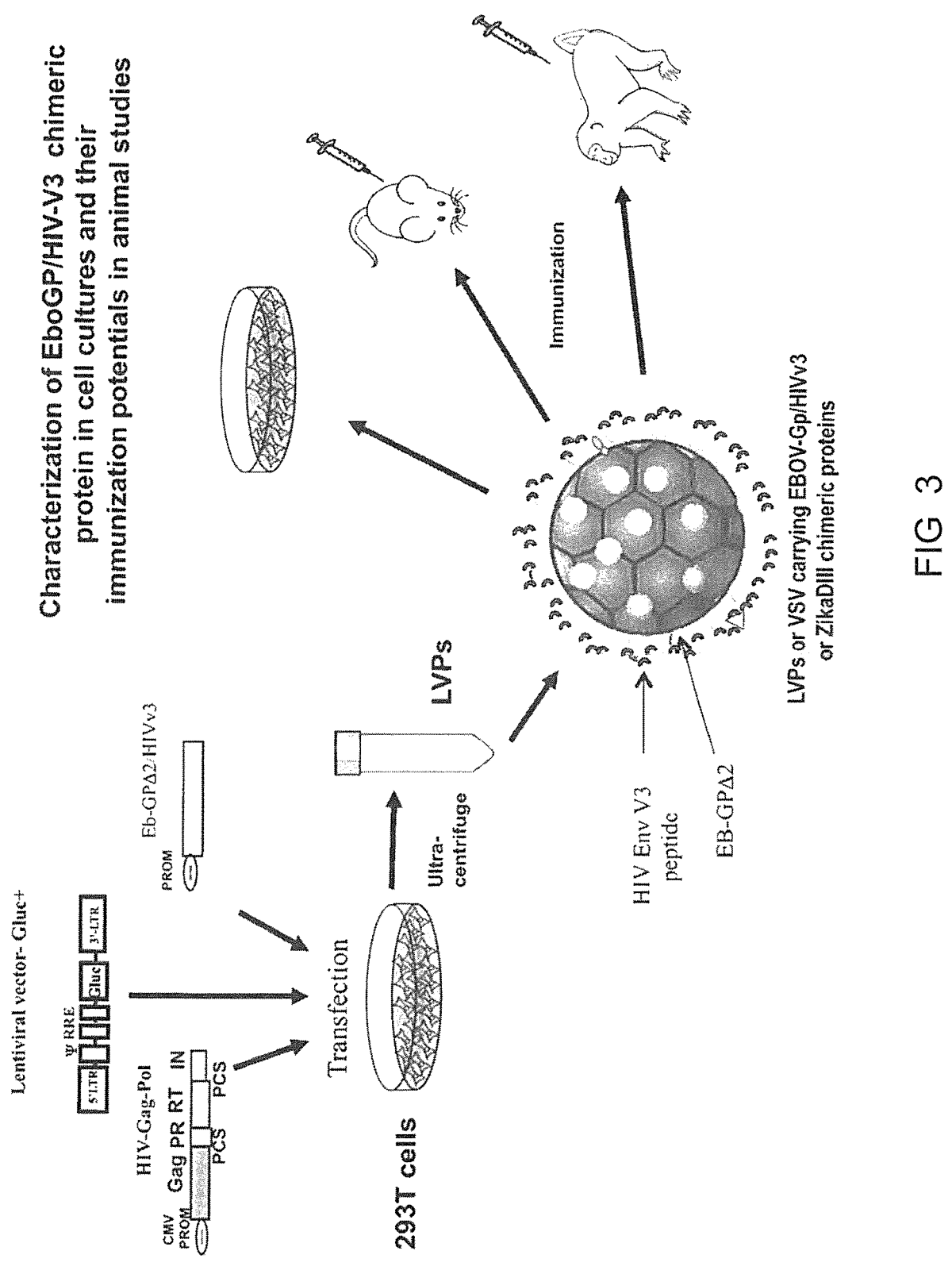

FIG. 3. Generation and characterization of Lentiviral particles carrying EboGP/HIV-v3 or EboGP/ZikaDIII chimeric fusion proteins. 293T cells were co-transfected by EboGP/HIV-v3 or EboGP/ZikaDIII expressor, the HIV-1 packaging plasmid CMV-HIV-Gag-Pol, and a lentiviral vector encoding for the *Gaussia* luciferase (Gluc) gene (2). 48 hrs post-transfection, cell culture supernatants were collected and pseudovirions were purified from the supernatant by ultracentrifugation (32,000 rpm) for 2 hrs. The pelleted viruses were resuspended in PBS, and used for cell culture infection assays and in animal immunization studies.

Figure 4:
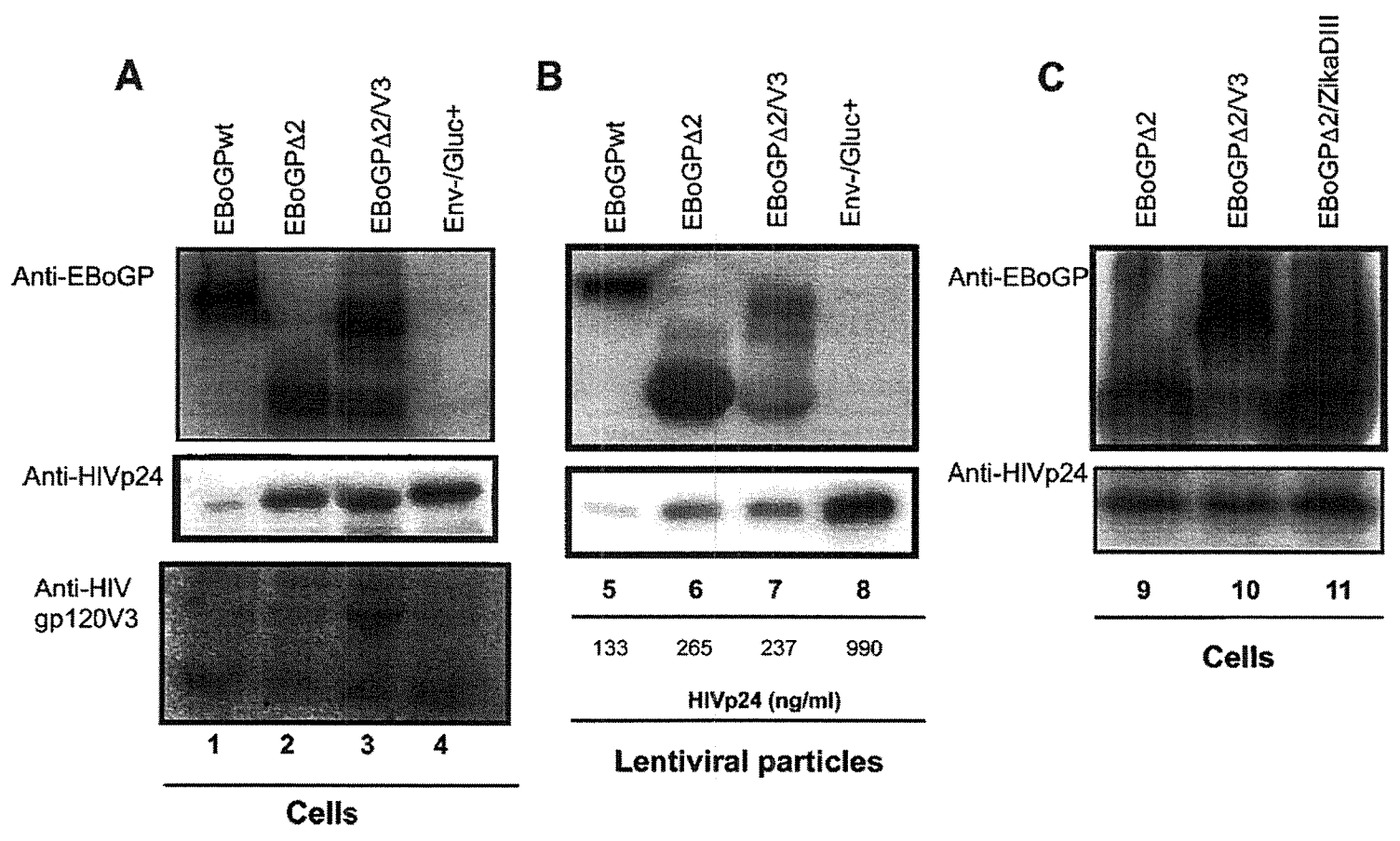

FIG. 4. Detection of EboGP/HIV-v3 or -ZikaDIII region chimeric protein in cells and in Lentiviral particles. To examine the expression and incorporation of EboGPΔ2/HIV-v3 chimeric proteins, both transfected cells and the produced lentiviral particles were lysed and analyzed by SDS-PAGE and Western blot with a mouse anti-EboGP (FIGS. 4A and B, upper panel), or anti-HIVGP-V3 antibodies (FIG. 4A, lower panel). The EboGPΔ2/ZikaDIII incorporation in the lentiviral particles were checked with a mouse anti-EboGP antibody (FIG. 4C, upper panel) the slower migrating bands indicating that the EboGP/ZikaDIII protein (FIG. 4C, upper panel, lanes 11). Meanwhile, the HIV capsid Gagp24 protein was detected in all of the cell lysates and the pelleted lentiviral particles by rabbit anti-p24 antibodies (FIG. 1A-C, middle panel).

FIG. 5. EboGP/HIV-v3 pseudotyped lentiviral particles (LVPs) can efficiently infect TZMB1 cells but not C8166 T cells. Equal amounts of pseudotype LVPs, as indicated in figure, were tested for the virus-entry ability of each EboGP-based chimeric fusion protein in TZMB2 cells, and T lymphoid cell line (C8166 T cells). At Day 1 and 3 post-infection, supernatants were collected and measured for Gluc activity and HIVp24 antigen levels.

Figure 6:
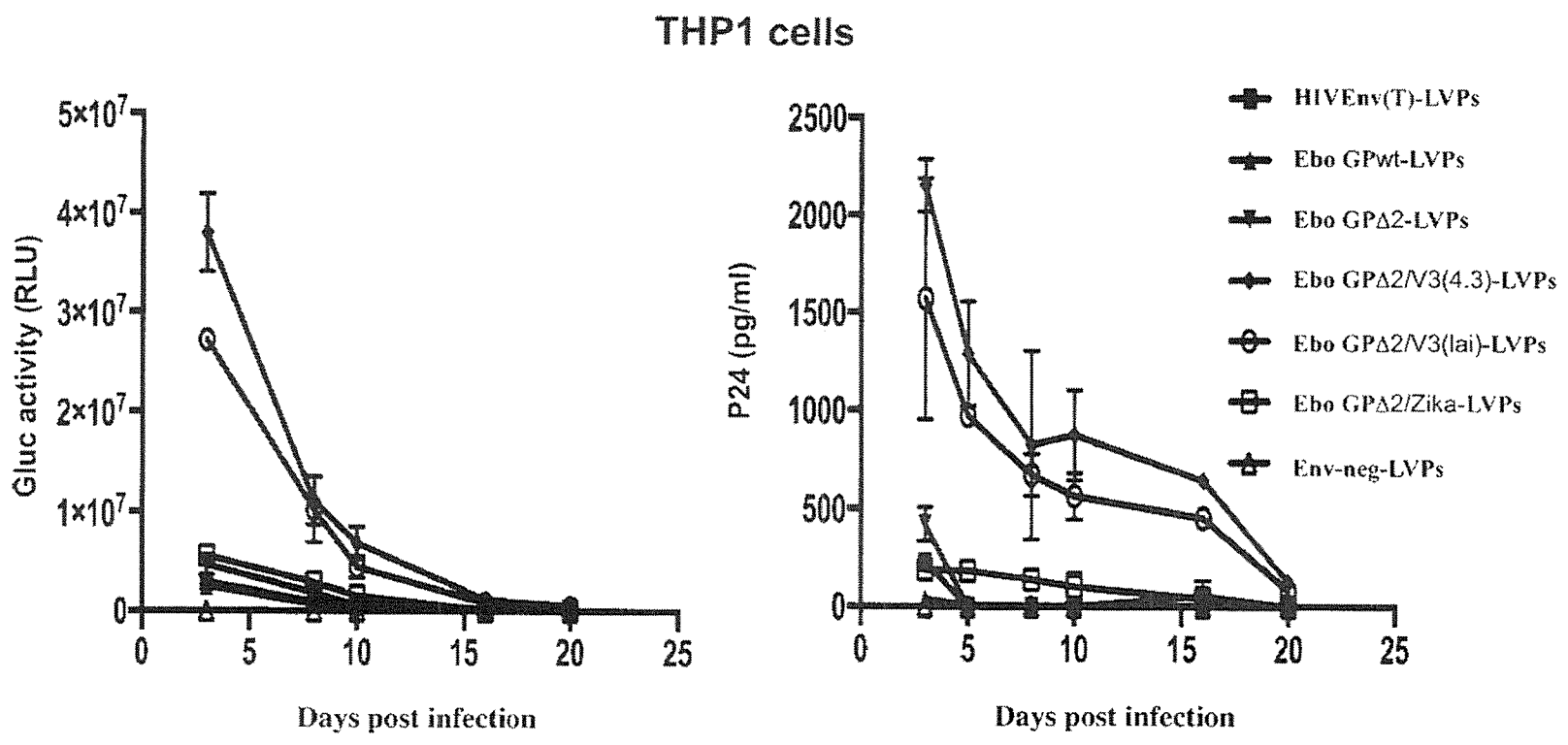

FIG. 6. EboGP/HIV-v3 pseudotyped LVPs can efficiently infect THP1 cells. To test the virus entry ability of EboGP/v3 pseudotyped LVPs in human monocytic cell line (THP1 cells), equal amounts of pseudotyped LVPs, as indicated in figure, were used to infect THP1 cell line. At different time intervals, supernatants were collected and measured for Gluc activity and HIVp24 antigen levels.

Figure 7:
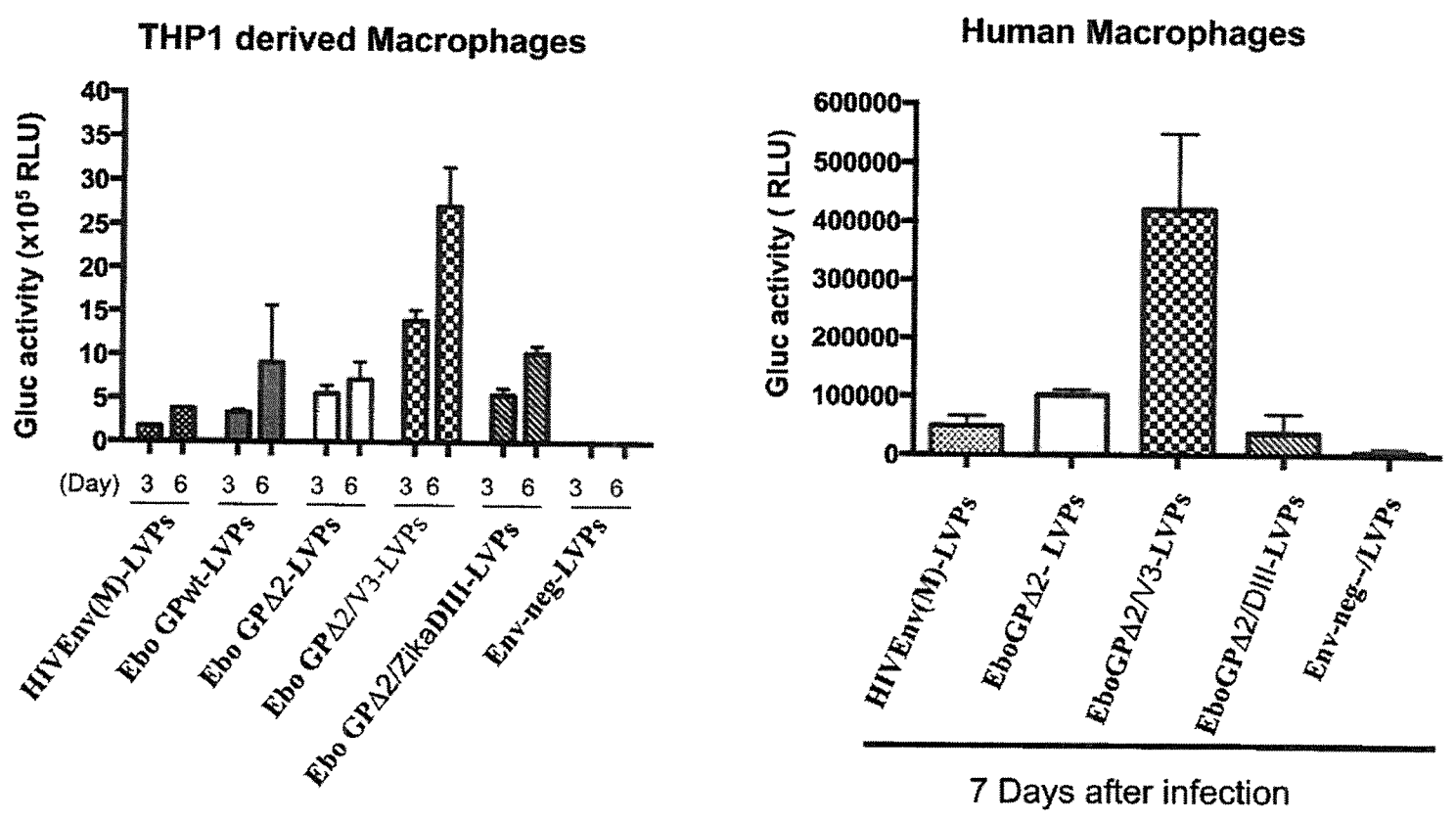

FIG. 7. EboGP/HIV-v3 pseudotyped LVPs can efficiently infect THP1 derived macrophages and primary human monocyte derived macrophages. To assess the virus-entry ability of EboGP/v3 pseudotyped LVPs in antigen presenting cells, equal amounts of psuedotyped LVPs, as indicated in figure, were used to infect THP1-derived macrophages and primary human monocyte derived macrophages. At various days postinfection (as indicated), supernatants were collected and measured for Gluc activity levels.

Figure 8:
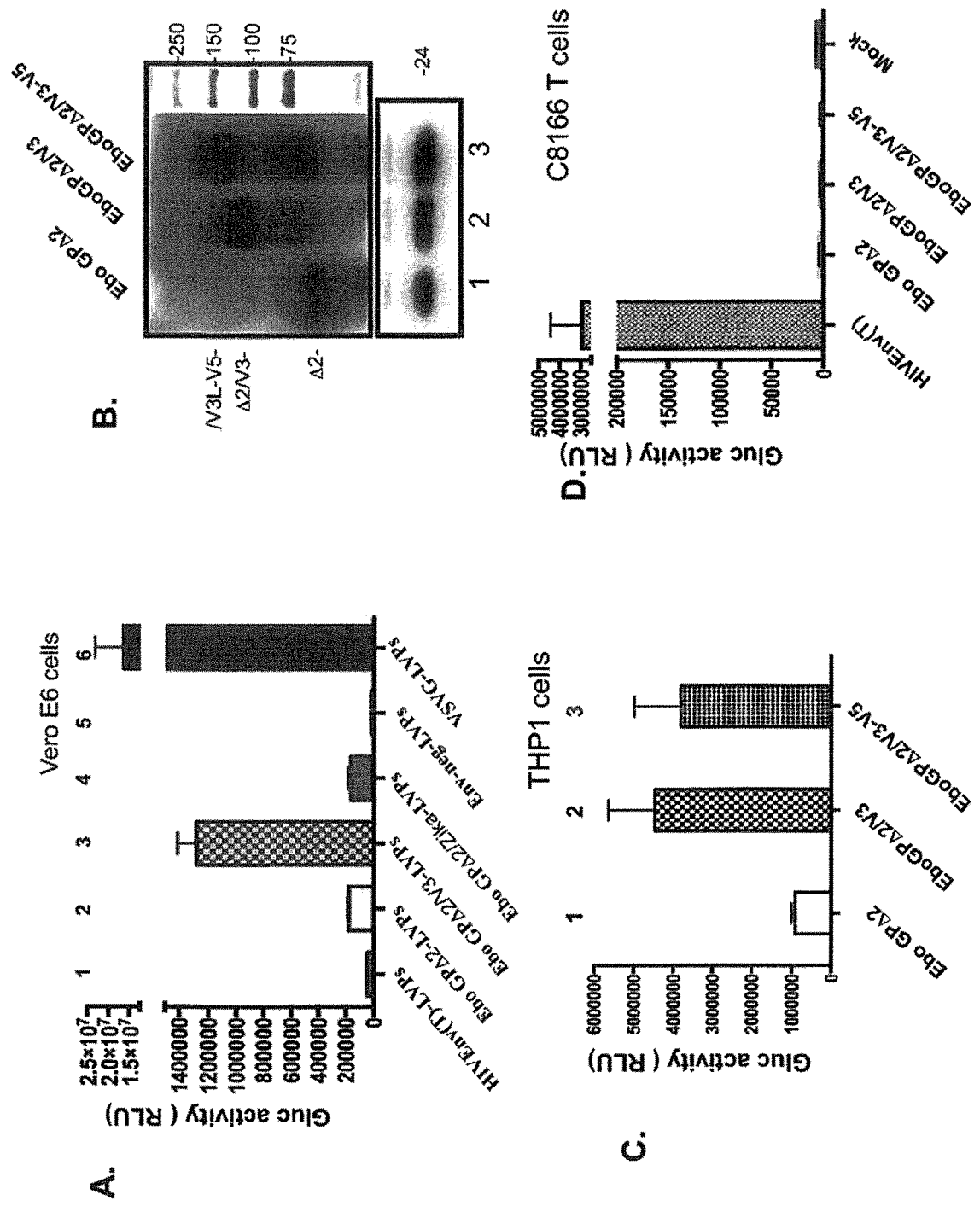

FIG. 8. A) Infection of EboGP/HIV-v3 pseudotyped LVPs in Vero E6 cells. B) Expression of EboGP/HIV-v3-v5 fusion protein. C and D) Infection of EboGP/HIV-V3 and EboGP/HIV-v3-v5 LVPs in THP1 cells but not C8166 T cells. A) shows EboGP/HIV-v3 pseudotyped LVPs can more efficiently infect Vero E6 cells, an FDA-approved cell line for vaccine production. Expression of EboGP/HIV-v3-v5 fusion protein in transfected 293T cells are shown in (B). (C and D) show that both EboGP/HIV-v3 and EboGP/HIV-v3-v5 pseudotyped LVPs are able to infect a human monocytic cell line (THP1) cells, but not CD4+ C8166 T cells.

Figure 9:
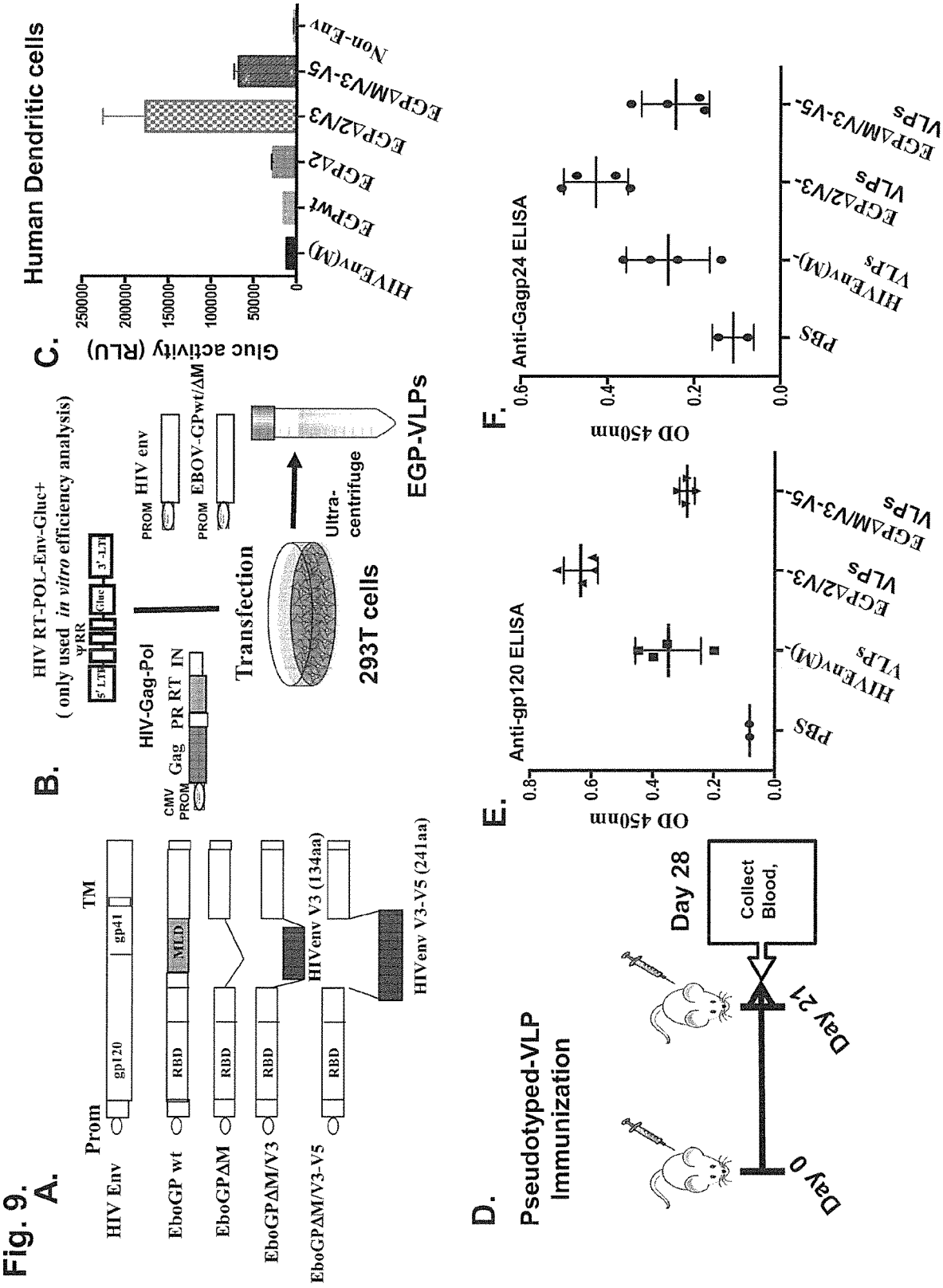

FIG. 9. The presence of EboGPΔM/V3 on the HIV LVPs greatly facilitates virus entry into human dendritic cells and immunogenicity of HIV LVPs. A) Schematic structures of mammalian cell expressing plasmids encode genes for HIV envelope glycoprotein or different Ebola envelop glycoprotein (EboGP) (including genes encoding EboGPwt, EboGPΔM, EboGPΔM/V3, and EboGPΔM/V3-V5 fusion proteins). In EboGPΔM/V3 fusion protein, a 134 amino acid polypeptide derived from HIV Env (from pNL4.3 strain) was inserted into EboGPΔM glycoprotein. B) Experimental procedures of the production of HIVEnv(M) or EboGPΔM/V3-pseudotyped HIV virus like particles (VLPs) in 293T cells. Gluc: Gaussia luciferase. C) Virus entry efficiency of Different pseudotyped VLPs in human monocyte-derived dendritic cells (MDDCs) and D) Schematic of the HIV Env or EboGP-pseudotyped HIV VLP immunization protocol in mice. The BALB/c mice were injected subcutaneously with 100 ng of HIVgp-VLPs, or each of pseudotyped VLPs. At 21 days post-immunization, mice were boosted with same amounts of VLPs, and sera were collected at 28 days of post-immunization for anti-HIV antibody measurement. E and F) The anti-HIVgp120 and anti-HIVp24 antibody levels in the sera of immunized BALB/c mice were measured by corresponding ELISAs. The values shown were the average levels of each group from 4 mice (except 2 mice in PBS injected group).

FIG. 10. Potent anti-HIV immune responses induced by rVSV co-expressing EboGPΔM/V3 and HIV Env, compared to rVSVHIVEnv/VSVG, rVSVHIVEnv/EboGPwt. A) Schematic structures of recombinant vesicular stomatitis virus (rVSV) vector co-expressing HIV envelop glycoprotein and VSVG (a), rVSV co-expressing HIV envelop glycoprotein and the wild type EboGPwt (b) or rVSV co-expressing HIV envelop glycoprotein and EboGPΔM/V3 (c). Each rVSV virus was rescued in VeroE6 by using a reverse genetics technology (47). Then, each rVSV stock was produced in VeroE6 cells and concentrated by ultracentrifugation, and virus titers were titrated in Vero E6 cells. B) Schematic plan of the HIV Env/EboGP-co-expressed rVSV immunization protocol in mice. Briefly, the BALB/c mice were injected subcutaneously with 1×106 TCID50 of each of rVSV-HIVEnv/VSVG, rVSV-HIVEnv/EboGPwt, or rVSV-HIVEnv/EboGPΔM/V3, as indicated. C) At 35 days post-immunization, mice were sacrificed, and sera were collected. The anti-HIVgp120 antibody levels in the sera of immunized BALB/c mice with different rVSVs were measured by anti-HIVgp120 ELISAs. The values shown were the average levels of each group from 4 mice.

Figure 11:
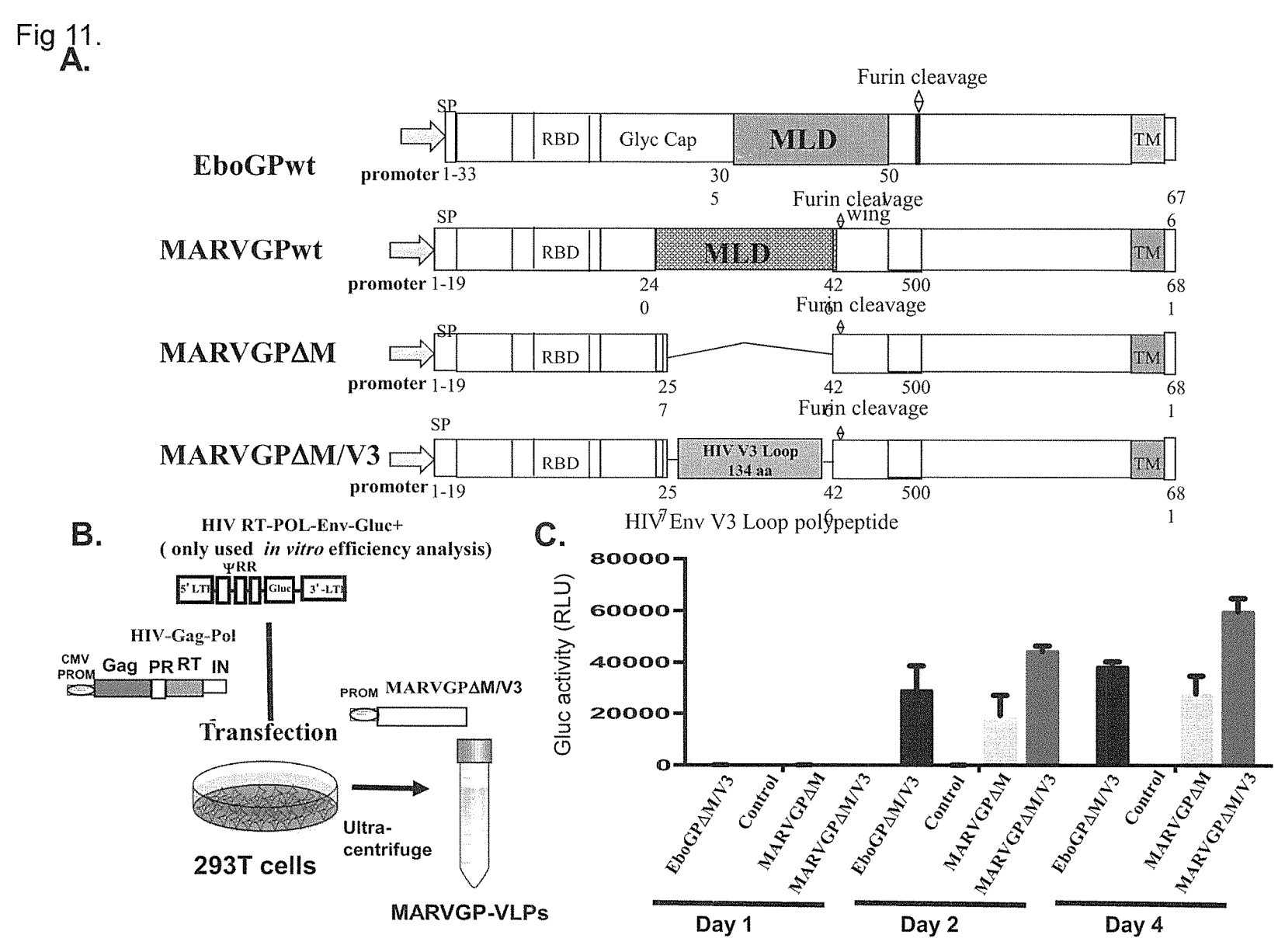

FIG. 11. Generation of Marburg virus glycoprotein (MARVGP)/HIV-V3 chimeric protein and its role in virus entry. A) MARVGP Gene and MLD-deleted (deletion encompassing aa 257 to 425) A MARVGP MLD-deleted gene sequences (the sequences shown in Table 3) were inserted into a mammalian cell expression vector, and named MARVGPΔM. To construct MARVGPΔM/V3 chimeric protein expressor, PCR amplified gene sequences (termed as HIVv3, which are shown in Table 2) were inserted into MLD-deleted MARVGP gene, and cloned into the mammalian cell expression vector, designated as MARVGPΔM/HIV-v3. B) To produced MARVGPΔM- or MARVGPΔM/HIV-v3-pseudotyped HIV virus like particles (VLPs), each plasmids were co-transfected with the HIV-1 packaging plasmid CMV-HIV-Gag-Pol, and a lentiviral vector encoding for the Gaussia luciferase (Gluc) gene (2). 48 hrs post-transfection, cell culture supernatants were collected and pseudovirions were purified from the supernatant by ultracentrifugation (32,000 rpm) for 2 hrs. The pelleted viruses were resuspended in PBS, and used for cell culture infection assays. C) Equal amounts of pseudotype VLPs, as indicated in figure, were tested for the virus-entry ability of each EboGPΔM/V3-, MARVGPΔM-, MARVGPΔM/V3-pseudotyped were used to infect TZMB2 cells. At Day 1, 2, and 3 post-infection, supernatants were collected and measured for Gluc activities.

Table 1. Sequence of EboGPopt-delta2. The nucleotide sequence (SEQ ID No: 1) represents a codon-optimized MLD-deleted EboGP gene sequences (SEQ ID No: 2). The gene sequence encoding mucin like domain (encompassing aa 306 to 483) has been deleted.

Table 2. Sequence of inserted HIV V3 region (SEQ ID No: 3 is nucleotide sequence; SEQ ID No: 4 is peptide sequence); Sequence of inserted HIV V3-V5 region (SEQ ID No: 5 is nucleotide sequence; SEQ ID No: 6 is peptide sequence); Sequence of inserted Zika DIII region (SEQ ID No: 7 is nucleotide sequence; SEQ ID No:8 is peptide sequence). The inserted gene sequence of HIV V3 region represents the partial gene sequence (encompassing aa231 to 365) of envelope glycoprotein (GP) gene from HIV strain pNL4.3 strain. The inserted HIV V3-V5 region sequence represents the partial gene sequence (aa231 to 471) of HIV pNL4.3 strain envelope glycoprotein (GP). The inserted immunoglobulin-like segment (DIII) sequence of Zika virus envelope glycoprotein is the synthesized gene sequence encompassing aa 303 to 404 of Zika envelope glycoprotein (GP).

Table 3. Sequence of MARVGPΔM. The sequence represents an MLD-deleted EboGP gene sequence (SEQ ID No: 9). The gene sequence encoding mucin like domain (encompassing aa 257 to 425) has been deleted.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As discussed herein, we have developed a series of Marburgvirus envelope glycoprotein (MarvGP)-based and Ebolavirus envelope glycoprotein (EboGP)-based chimeric fusion proteins, including EboGP/HIV-v3, EboGP/HIV-v3-v5, and EboGP/ZikaDIII chimeric fusion proteins, that are still able to maintain an efficient EboGP-mediated virus entry in various cell types including human antigen-presenting cells (APCs), macrophages, while presenting large viral polypeptides, such as HIV Env v3-v5 domain (as large as 241 aa), at the apex and the sides of each EboGP monomer to elicit robust host immune responses.

Furthermore, envelope glycoproteins (GPs) from other Filoviridae family can be also used to develop the same technology as the EboGP-based chimeric fusion protein technology for the novel vaccine approaches, gene therapies and anti-cancer strategies. Beside EboGP and MarvGP, which are used in this invention, the envelope glycoproteins from other Filoviridae family, including Ebolavirus (Sudan Ebolavirus, Bundibugyo Ebolavirus), Marburgvirus (Marburg virus (see in FIG. 11), and Ravnvirus) and Cuevavirus (16), also have the mucin like domain (MLD) and similar glycoprotein structures. Accordingly, EboGPs from other Filoviridae family can also be used to develop Filoviridae glycoprotein based (FiloGP-based) chimeric fusion protein technology for novel vaccine approaches, gene therapies and anti-cancer strategies, as discussed herein.

Accordingly, reference is made to FiloGP-based chimeric fusion proteins which refer to insertion of a peptide of interest into the mucin like domain of a Filoviridae virus known to have or suspected of having a mucin-like domain within the glycoprotein of the respective virus.

It is further of note that the expression "glycoprotein" or "GP" does not necessarily mean that the peptide or protein being referred to is "full-length" glycoprotein ("full length" as used herein refers to the region of the glycoprotein excluding the mucin-like domain which as discussed herein has a peptide inserted therein and in some embodiments the peptide replaces at least part of the mucin-like domain). Rather, as used herein, "glycoprotein" or "GP" refers to the fact that the glycoprotein is capable of functioning in the formation of virus-like particles and/or viral vector(s), that is, that the glycoprotein is a "functional" glycoprotein.

This invention demonstrates the feasibility of a MarvGP-based chimeric fusion and an EboGP-based chimeric fusion technology as a novel vaccine approach against different microbial pathogens, including that in human and animals, and against cancers.

Specifically, as discussed herein, foreign or antigenic peptides may be inserted into the mucin-like domain. As discussed herein, this insertion may be accompanied by a corresponding deletion of native amino acid sequence of the mucin-like domain within a Filoviridae virus glycoprotein, for example, the MarvGP peptide or the EbolaGP peptide although as discussed herein this may not be necessary. As discussed herein, the mucin-like domain is generally accepted as encompassing residues 305 or 308 to 501 of the EboGP peptide sequence and amino acid residues 257-501 of the Marburg virus (10). As shown herein, we have deleted amino acids 306 to 483 of the EboGP and amino acids 257-425 of the MarvGP peptide. For example, the deletion of 178 amino acids permits the insertion of larger peptides, such as the HIV V3-V5 domain which is 241 amino acids. Specifically, deletion of these 178 amino acids and replacement thereof with an antigenic peptide of interest results in the peptide of interest being presented or displayed or expressed at the apex and sides of the glycoprotein monomer. Surprisingly, this placement does not affect EboGP cell entry and also exposes the antigenic peptide of interest to the host immune system, as discussed below.

As will be appreciated by one of skill in the art, other suitable deletions can be easily determined by a variety of means well known to those of skill in the art and are within the scope of the invention. That is, in-frame insertions of small peptides without deletion of any amino acids of the mucin-like domain will be tolerated and will result in the presentation of the small peptide at the sides and apex of the FiloGP domain for example EboGP or MarvGP as discussed herein. This is supported by the fact that the insertion of a 241 amino acid peptide into a 178 amino acid deletion of the mucin-like domain was tolerated and the transgenic EboGP peptide was capable of cell entry and presented the peptide of interest at the side(s) and apex of the EboGP peptide, as discussed herein. Similarly, deletions smaller than the 178 amino acid deletion or somewhat larger than the 178 amino acid deletion may be used within the invention, provided that folding of the domains upstream and downstream of the mucin-like domain is not affected and so that the inserted peptide is still presented at the apex and sides of the EboGP peptide.

Accordingly, as used herein, the phrase "comprising a peptide of interest inserted in-frame into the mucin domain of the EboGP protein" refers to a peptide that has been inserted in frame into the mucin-like domain with or without deletion of all or part or a significant portion or a tolerated portion of the native amino acid sequence of the mucin-like domain, specifically, amino acids 305 to 501 of the EboGP native peptide sequence or amino acids 257 to 501 of the MarvGP native peptide sequence. One example of deletion of a tolerated portion of the mucin-like domain is amino acids 306 to 483 of the EboGP which as discussed herein permits presentation of the inserted peptide at the side(s) and apex of the EboGP peptide. Another example is amino acids 257-425 of MarvGP, as discussed herein. As discussed herein and as will be apparent to one of skill in the art, other tolerated deletions will not alter the properties of the other functional domains of the FiloGP peptide, for example, the EboGP peptide or MarvGP, in particular, the ability of the MarvGP or EboGP fusion protein to enter APC cells and of the presentation of the inserted peptide at the side(s) and apex of the FiloGP fusion protein as discussed herein and as shown in for example FIG. 1.

It is also important to note that insertion of a peptide into the mucin-like domain without deletion is an in-frame insertion that may be made at a variety of positions so that the protein of interest is presented at the side(s) and apex of the FiloGP fusion peptide.

As discussed above, it is important to note that the deletion of 178 amino acids was sufficient for insertion of a much larger peptide (241 amino acids). This in turn indicates that insertion of larger peptides into the mucin-like domain are possible, that is, that the mucin-like domain will tolerate insertion of larger peptides. Accordingly, it is important to note that for example the 178 amino acid deletion will also tolerate insertion of much smaller peptides and may also be used for the presentation of smaller peptides such as those of 15 amino acids or less or of 9 amino acids or less.

Specifically, as discussed herein, the deletion of the mucin-like domain is known to be tolerated by the EboGP protein without affecting cell entry. However, what was not known and what is surprising is that insertion of a foreign or non-native peptide sequence into the mucin-like domain does not affect the functioning of the other domains of the EboGP protein or MarvGP protein and the inserted peptide sequence is presented at the side(s) and apex of the MarvGP fusion peptide or EboGP fusion peptide, thereby making the FiloGP protein for example EboGP protein or MarvGP protein an ideal vehicle for expression and presentation of peptides of interest, that is, antigenic peptides.

As will be appreciated by one of skill in the art, any suitable peptide can be inserted into the mucin-like domain of the FiloGP peptide or protein as discussed herein. However, because of the way in which the inserted peptides are presented on the FiloGP fusion peptide, for example, the EboGP fusion peptide or the MarvGP fusion peptide and because of the delivery of the fusion protein into antigen presenting cells (APC), this system is particularly well suited for generation of an immune response for example antibodies against peptides such as intracellular proteins or domains that are structurally hidden within a protein in their native state. Other examples of suitable inserted peptides are discussed herein. Alternatively, different polypeptides from HIV, influenza virus or other high-risk viruses can be expressed as FiloGP-based chimeric fusion proteins, as discussed herein.

As known by those of skill in the art, dendritic cells (DCs) are one of the most potent specialized antigen-presenting cells (APCs) as they form a critical link between the innate and adaptive immune responses (25). After being stimulated or after antigen uptake, DCs initiate immune responses via the secretion of chemokines and pro-inflammatory cytokines and the up-regulation of a variety of costimulatory and chemokine receptors. After maturation, they efficiently present antigens and initiate both innate and adaptive immune responses (9, 12). In addition, DCs can release specific cytokines to guide and enhance Th1 and/or Th2 arm(s) of the T cell responses to pathogens.

As discussed herein, this demonstrates the feasibility for inserting various heterologous large polypeptide, such as that derived from HIV, Zika virus, and other pathogens, as well as that from cancer specific peptides, into the mucin like domain (MLD) and/or replace the MLD of the FiloGP for example the EboGP or MarvGP as novel vaccine approaches, for example for the preparation of a vaccine against HIV-1 infection.

For example, the mucin insertion system may be used for the generation of an anti-cancer vaccine. Specifically, there are some mutations already found in some tumor-related protein or receptor(s) in late stage patients being treated with anti-cancer chemotherapy (34). It is possible to insert these mutated polypeptides into the mucin-like domain of for example EboGP or MarvGP to generate a vaccine against cancer. In this manner, any tumor specific proteins or biomarkers may be used in combination with the mucin-like insertion system to generate anti-cancer vaccine.

Our study demonstrates that the mucin like domain (MLD) of EboGP can be replaced by various heterologous polypeptides, including HIV V3 loop peptide, HIV V3-V5 (241aa), or ZikaDIII peptide. Also, because the mucin-like domain of the EboGP is located at the apex and the sides of each EboGP monomer, large heterologous polypeptides will also be fully exposed at the apex and the sides of each glycoprotein monomer (FIGS. 1E and F). Thus, they will be fully exposed to the host immune system and elicit effective immune responses because the apex and the side(s) of for example the EboGP will be on the outside of the virus-like particles and also on the APCs, as discussed herein.

Accordingly, the MLD insertion system described herein can be used for FiloGP-based chimeric fusion protein-mediated virus entry in human Dendritic cells (DCs) which as discussed herein will induce an efficient immune response.

Also described herein is the incorporation of these FiloGP-based chimeric fusion proteins in different viral vectors or other forms of enveloped vesicles to achieve a specific, and more efficient antigen-presenting cell entry method for broad kinds of vaccine and therapeutic uses. The placement of large polypeptides, including HIV v3 regions (134 aa), in the position of the mucin like domain (MLD) of EboGP surprisingly did not negatively impact the EboGP's targeting and the virus' ability to enter various cells including human antigen-presenting cells (APCs) and macrophages, but also achieved a more efficient cell entry, as discussed below.

As will be apparent to one of skill in the art, the FiloGP-based chimeric fusion protein can be used in combination with any of the variety of known live, attenuated vaccines vectors, including vesicular stomatitis virus (VSV) (shown in FIG. 10), recombinant modified vaccinia Ankara (rMVA), a canarypox vector vaccine vectors, and other inactivated virus-like particles (VLPs).

Also described are dual action vaccines against Ebola viral infection and HIV infection or other emergent viral infections. The placement of large polypeptides, including HIV, Zika, influenza, or other emergent viral pathogens in the MLD-deleted EboGP generates a dual action vaccine against both Ebola viral infection and HIV infection or other emergent viral infections.

Also described herein is a potent and specific DC-targeting vaccine approach and/or other specific cell targeting gene therapeutic uses.

Specifically, the finding that insertion of HIV V3 region (134aa) is able to enhance EboGP targeting of APCs, such as macrophages demonstrates that the EboGP-based fusion techniques can be used as a potent and specific APCs including DCs) targeting vaccine approach, and can elicit a robust immune response. However, this also indicates that other specific cell targeting signals may be used in combination with the FiloGP fusion system to generate fusion glycoproteins capable of targeting specific cells. Furthermore, the results indicate that the HIV V3 region can be used with other fusion systems or expression systems for cell targeting, specifically, targeting of APCs.

While not wishing to be bound to a specific theory or hypothesis, it is noted that the inserted V3-V5 domain contains a CD4 binding region and a coreceptor binding determinant, which is critical for binding to cell receptors and initiating HIV infection. The use of the V3-V5 domain as an antigen in the fusion is aimed to elicit neutralizing antibodies blocking HIV infection. However, this fusion has the unique advantage of being expressed at the side(s) and apex of FiloGP for example EboGP or MarvGP which will in turn increase the exposure of the V3-V5 domain to the host immune system and specifically to the antigen presenting cells.

According to an aspect of the invention, there is provided a fusion protein comprising a peptide of interest inserted in the mucin-like domain of a Filoviridae Virus glycoprotein.

In some embodiments of the invention, the Filoviridae virus is Ebola virus or Marburg virus.

In some embodiments, the mucin-like domain comprises amino acids 305-501 of the Ebola Virus glycoprotein.

In some embodiments, the mucin-like domain consists of amino acids 305-501 of the Ebola virus glycoprotein.

In some embodiments, the mucin-like domain comprises amino acids 257-501 of Marburg virus glycoprotein.

In some embodiments, the mucin-like domain consists of amino acids 257-501 of Marburg virus glycoprotein.

In some embodiments, the mucin-like domain is a tolerated deletion of the mucin-like domain. That is, in some embodiments, the protein of interest is not only inserted in frame into the mucin-like domain of the Filoviridae glycoprotein, the peptide or protein of interest also replaces at least some of the mucin-like domain. That is, as discussed below, the peptide or protein of interest is inserted in frame into a tolerated deletion of the mucin-like domain, as discussed herein.

In some embodiments, the fusion protein further comprises the HIV glycoprotein V3 and/or v3-v5 domain.

In some embodiments, there is provided a nucleic acid encoding the fusion protein described above.

In some embodiments, there is provided a virus-like particle comprising the fusion protein described above.

According to another aspect of the invention, there is provided a method of targeting a peptide of interest to an antigen presenting cell comprising:

providing a virus-like particle comprising as glycoprotein a Filoviridae Virus glycoprotein fusion protein comprising a protein of interest inserted in the mucin-like domain of the Filoviridae Virus glycoprotein; and immunizing an individual in need of immunization against the peptide of interest with an effective amount of the virus-like particle.

In some embodiments, the Filoviridae virus is Ebola virus or Marburg virus.

According to another aspect of the invention, there is provided use of a virus-like particle comprising as glycoprotein a Filoviridae Virus glycoprotein fusion protein comprising a protein of interest inserted in the mucin-like domain of the Filoviridae Virus glycoprotein for targeting a peptide of interest to an antigen presenting cell.

In some embodiments of the invention, the Filoviridae virus is Ebola virus or Marburg virus.

According to another aspect of the invention, there is provided a method of eliciting an enhanced immune response against a peptide of interest comprising:

providing a virus-like particle comprising as glycoprotein a Filoviridae Virus glycoprotein fusion protein comprising a protein of interest inserted in the mucin-like domain of the Filoviridae Virus glycoprotein; and immunizing an individual in need of immunization against the peptide of interest with an effective amount of the virus-like particle.

In some embodiments, the Filoviridae virus is Ebola virus or Marburg virus.

According to another aspect of the invention, there is provided use of a Filoviridae Virus glycoprotein fusion protein comprising a protein of interest inserted in the mucin-like domain of the Filoviridae Virus glycoprotein for eliciting an enhanced or increased immune response against a peptide of interest.

As will be appreciated by one of skill in the art, the increased or enhanced immune response may be in an individual, in particular, an individual in need of immunization against the peptide of interest, wherein the individual may be a human.

In some embodiments, the Filoviridae virus is Ebola virus or Marburg virus.

According to another aspect of the invention, there is provided a method of targeting a peptide of interest to an antigen presenting cell comprising:

preparing a fusion protein comprising a Filoviridae Virus glycoprotein comprising a peptide of interest inserted in the mucin-like domain of the Filoviridae Virus glycoprotein;

assembling virus-like particles comprising the fusion protein; and immunizing an individual in need of immunization against the peptide of interest with an effective amount of the virus-like particle.

In some embodiments, the Filoviridae virus is Ebola virus or Marburg virus.

According to another aspect of the invention, there is provided use of a fusion protein comprising a Filoviridae Virus glycoprotein comprising a peptide of interest inserted in the mucin-like domain of the Filoviridae Virus glycoprotein for targeting the peptide of interest to an antigen presenting cell.

In some embodiments, the Filoviridae virus is Ebola virus or Marburg virus.

According to another aspect of the invention, there is provided a method of eliciting an enhanced or increased immune response against a peptide of interest comprising:

preparing a fusion protein comprising an Filoviridae Virus glycoprotein comprising a peptide of interest inserted in the mucin-like domain of the Filoviridae Virus glycoprotein;

assembling virus-like particles comprising the fusion protein; and immunizing an individual in need of immunization against the peptide of interest with an effective amount of the virus-like particle.

In some embodiments, the Filoviridae virus is Ebola virus or Marburg virus.

As will be appreciated by one of skill in the art, the immune response generated by the fusion protein is increased or enhanced over the immune response that would be generated in a control individual, that is, an individual of similar age or condition as the immunized individual, immunized with the peptide of interest alone.

According to another aspect of the invention, there is provided use of a fusion protein comprising a Filoviridae Virus glycoprotein comprising a peptide of interest inserted in the mucin-like domain of the Filoviridae Virus glycoprotein for eliciting an enhanced or increased immune response against a peptide of interest.

In some embodiments, the Filoviridae virus is Ebola virus or Marburg virus.

According to a further aspect of the invention, there is provided a method of targeting a peptide of interest to an antigen presenting cell comprising:

preparing a fusion protein comprising HIV V3 or V3-V5 domain fused to the peptide of interest;

assembling virus-like particles comprising the fusion protein; and immunizing an individual in need of immunization against the peptide of interest with an effective amount of the virus-like particle.

According to a further aspect of the invention, there is provided use of an HIV V3 or V3-V5 domain for targeting a peptide of interest to an antigen presenting cell.

In some embodiments, the fusion peptide further comprises Filoviridae Virus glycoprotein, for example Ebola virus glycoprotein or Marburg virus glycoprotein.

In some embodiments, the peptide of interest and the HIV V3 or V3-V5 domain are inserted into the mucin-like domain of a Filoviridae Virus glycoprotein, for example Ebola virus glycoprotein or Marburg virus glycoprotein.

In some embodiments, the peptide of interest and the HIV V3 or V3-V5 domain are inserted into a tolerated deletion of the mucin-like domain of a Filoviridae Virus glycoprotein, for example Ebola virus glycoprotein or Marburg virus glycoprotein.

The invention will now be further described by way of examples; however, the invention is not necessarily limited to the examples.

Example 1. Generation of EboGP/HIV-v3 and EboGP/ZikaDIII Chimeric Fusion Proteins and their Expression Previous studies have showed that the mucin-like region of the Ebola-GP (EboGP) is located at the apex and the sides of each glycoprotein monomer (39). To determine if replacing this MLD region with a heterologous polypeptide(s) would affect the functional integrity of EBOV-GP (FIGS. 1E and F), we constructed an EboGPΔ2 expressing plasmid by deleting the mucin like region (from amino acid 305 to 485) (Table 1) and created an ApaI site and an XbaI site in an EBoGPwt expressor (44). In EbGPΔ2/HIV-v3, EbGPΔ2/HIVv3-v5, and EbGPΔ2/ZikaDIII expressors, an HIV v3 loop peptide (134 amino acid (aa)), HIV v3-v5 loop peptide (241 aa) (FIG. 2; Table 2) or an Zika DIII region (102 aa) (45) (FIG. 2; Table 2) were inserted into EboGPΔ2 and replaced the mucin like region, respectively (FIG. 2).

To examine the expression of each Eb-GP chimeric protein and if they are still functional to mediate virus entry, we transfected each of these plasmids with a lentiviral-Gluc vector and the packaging plasmid (Δ8.2) into 293T cells, following the protocol described previously (44), as shown in FIG. 3. After 48 hrs of transfection, we collected the produced lentiviral particles (LVPs) from the supernatants in the culture, through ultracentrifugation (FIG. 3). Then the pelleted LVPs were lysed, and analyzed by SDS-PAGE and Western blot with a mouse anti-EBOV-GP1. As indicated in FIG. 4, the EboGPwt, EboGPΔ2 and each of EboGPΔ2/HIV-v3 and EboGPΔ2/ZikaDIII can be detected in both cells and lentiviral particles (FIG. 4, upper panel, lanes 1-3; 5-7; 9-11). Meanwhile, results showed that the HIV capsid Gagp24 protein was detected in the transfected cells, and pelleted lentiviral particles (FIG. 4, middle panel, lanes).

To check if the inserted HIV v3 loop peptide in the EbGPΔ2/HIV-v3 chimeric protein can be recognized by anti-HIVgp120 antibody, we processed an anti-HIV V3 antibody western blot, the result clearly shown only the EbGPΔ2/HIVv3 chimeric protein was recognized by a well known anti-V3 neutralizing antibody obtained from NIH (W0-07) (19) (FIG. 4A, lower panel, lane 3). Similarly, this data indicates the HIV V3 loop peptide in EbGPΔ2/HIV-v3 chimeric protein will be well exposed to the host immune system, and able to induce the neutralizing antibodies against HIV infection.

Example 2. Investigation of the Virus Entry Mediated by Each EboGP-Based Chimeric Fusion Proteins To test whether each EboGP-based chimeric fusion protein is able to mediate virus entry, equal amounts of EboGPwt, EboGPΔ2, or EboGPΔ2/HIV-v3 lentiviral vector particles (LVPs) (as adjusted by HIV Gagp24 levels) were used to infect TZMB2 cells (the HeLa cells expressing CD4+/CXCR4 and have integrated HIV-LTR-luciferase) and T lymphoid cell line (C8166 T cells). In parallel, a LVPs without any viral envelop glycoprotein (Env-/LVPs) were used as negative control. Results showed that both EboGPwt and EboGPΔ2 could infect TZMB2 cells, compared to the Env-/LVPs (FIG. 5A, compare bars 1 and 2 to bar 4). Surprisingly, LVPs pseudotyped with EboGPΔ2/HIV-v3 mediated infection even more efficiently than the LVPs pseudotyped with EboGPwt or EboGPΔ2 (FIG. 5A, compare bar 3 to bars 1 and 2). This result suggests that the replacement the MLD with HIV V3 loop region enhanced the cell entry ability of the fusion protein EboGPΔ2/HIV-v3.

The next question we asked whether insertion of V3 loop region could change the cell tropism. Since we know that T cells are resistant to EboGP-mediated virus entry (44), hence, we use each LVPs stock described above to infect T lymphoid cell line (C8166 T cells). Results revealed that while HIV Env (T-tropic) incorporated LVPs were able to infect C8166 T cells efficiently, both EBoGPΔ2, or EbGPΔ2/HIV-v3 LVPs only mediate very low levels of infection in C8166 T cells (FIG. 5B). These results clearly indicate that the replacement the MLD in HIV V3 loop region in EBoGP is able to increase virus entry in HeLa cells, but had no effect in T lymphocytes.

Example 3. Characterization of Infection of EbGPΔ2/HIV-v3-Pseudotyped LVPs in Macrophages Since the EboGP has a preference to target dendritic cells, monocytes and macrophages (25, 26), we next tested if the insertion of heterologous polypeptides could affect the EboGP's ability to infect monocytes and macrophages. Firstly, we used equal amounts of EboGPwt, EboGPΔ2, or EboGPΔ2/HIV-v3 LVPs to infect in a human monocytic cell line (THP1 cells)(3). At different time intervals, the supernatants were collected and measured for virus induced *Gaussia* luciferase (Gluc) activity and HIV Gagp24 antigen. Results revealed that significant high levels of Gluc activity and HIV Gagp24 antigen were detected from the EboGPΔ2/HIV-v3 pseudotyped LVPs infected THP1 cell culture (FIG. 6). The data also showed that the infection level of EboGPΔ2/ZikaDIII pseudotyped LVPs was almost comparable to that of EboGPwt or EboGPΔ2 pseudotyped LVPs (FIG. 6), suggesting that the insertion of ZikaDIII peptide in EboGPΔ2 did not significantly affect EboGPΔ2's virus entry efficiency. These data indicate that an EboGPΔ2/ZikaDIII fusion protein in a vaccination vector, such as VSV vector, can be used as a dual-action vaccination against Ebola virus and Zika virus infection. Also, using the same strategy, it is feasible to place Zika DI-II domain (193 aa) in the MLD domain of EboGPΔ2 to generate an even broader vaccine against other flavivirus family members, including dengue (DENV), yellow fever (YFV), West Nile (WNV), and Japanese encephalitis (JEV) virus infections, since the envelope glycoproteins from these flavivirus members share a highly conserved DI-II domain (6, 45).

We also further tested the infection of different EboGP-fusion protein pseudotyped LVPs in THP1 derived macrophages (FIG. 7A) and primary human monocyte derived macrophages (FIG. 7B). In parallel, a HIV macropage-tropic Env incorporated LVPs were (HIVEnv(M)-LVPs) included as control. From the data in FIG. 7, we conclude that 1) EboGPwt or EboGPΔ2 pseudotyped LVPs infections in both THP1 derived macrophages and the primary human monocyte derived macrophages were modestly more efficient than that of HIVEnv(M)-LVPs; 2) The infection of EboGPΔ2/HIV-v3 pseudotyped LVPs in both macrophages was significantly more efficient than other pseudotyped LVPs, while infection levels of EboGPΔ2/ZikaDIII pseudotyped LVPs was comparable to that of EboGPwt or EboGPΔ2 pseudotyped LVPs. This data indicates again that insertion of foreign polypeptides does not interfere with EboGPΔ2's macrophage entry ability. More interestingly, insertion of HIVv3 polypeptide in fact enhanced the macrophage-targeting efficiency of the fusion protein.

As discussed below, the EboGP-fusion proteins are able to efficient target cells that will be used for FDA approval cell line for vaccine production. It is known that Vero cell line, derived from monkey kidneys, is a U.S. FDA approved cell line to produce viral vaccine preparations for clinical use. Hence, we further tested the infection of different EboGP-fusion protein pseudotyped LVPs in Vero cells. At three days post-infection in Vero E6 cells, we collected the supernatant and measured the produced Gluc activity (FIG. 8A). As expected, VSV-pseudotyped LVPs very efficiently infected Vero cells, while HIVEnv(T)-LVPs were unable (FIG. 8A bar 8, and 1). EboGPΔ2- and EboGPΔ2/ZikaDIII-pseudotyped LVPs can also infect Vero E6 cells, while EboGPΔ2/HIV-v3 pseudotyped LVPs mediated significantly higher Gluc activity (FIG. 8A, compare bar 3 to bars 2 and 5). This indicates that EboGPΔ2/HIVv3 has strong Vero cell-targeting ability and it is suitable for use in Vero cells for various viral vaccine production for clinical use. Overall, these studies provide evidence that EboGPΔ2/HIV-v3 has more efficient targeting of antigen presenting cells, such as macrophages, as well as for FDA-approved vector producing cells, Vero cells. This is particularly important since when the EboGPΔ2/HIV-v3 was encoded in viral vector system, such as VSV vector, it will facilitate VSV replicate in Vero cells and produce large quantities of VSV particles, which can be subsequently used for animal studies and clinical trial. Meanwhile, the presence of EboGPΔ2/HIV-v3 can greatly enhance the host immune responses to any antigens expressed in VSV vector since it has strong ability to target the antigen presenting cells, such as macrophages, and dendritic cells.

Example 4. Characterization of the Expression of EbGPΔ2/HIVv3-v5 Chimeric Protein and its Ability to Mediated Virus Entry The next question we asked is whether an even larger polypeptide could also be inserted into MLD-deleted EboGP, and if that will also not interrupt EboGP's function. Hence, we inserted a 241 aa long peptide derived from HIV Env glycoprotein, encompassing the V3-V5 region, into the EboGPΔ2 expressor, named EbGPΔ2/HIVv3-v5 (FIG. 2; the sequence is shown in Table 2), and tested its expression in transfected 293T cells by SDS-PAGE and Western blot with a mouse anti-EBOV-GP1. Results clearly showed that EbGPΔ2/HIVv3-v5 protein migrated at a lower rate than that of EbGPΔ2/HIV-v3 because v3-v5 is a larger polypeptide (241aa) compared to V3 one (134 aa) (FIG. 8B, compare lane 3 to lane 2).

To test whether each EboGP-based chimeric fusion protein is able to mediate virus entry, equal amounts of EboGPΔ2, EboGPΔ2/HIV-v3, or EbGPΔ2/HIVv3-v5 pseudotyped LVPs) (as adjusted by HIV Gagp24 levels) were used to infect THP1 cells. In THP1 cells, the infection of EbGPΔ2/HIVv3-v5 LVPs (FIG. 8C, bar 3) was slightly less efficient than that of EbGPΔ2/HIVv3 (bar 2), but was more effective than that of EbGPΔ2 pseudotyped LVPs (bar 1), suggesting that insertion of a larger peptide derived from HIV Env glycoprotein (241 aa, almost account for 50% of native HIV gp120), still maintain the similar efficient EboGP's virus entry ability in THP1 cells, as compared to EbGPΔ2 pseudotyped LVPs. These results provide evidence that the EboGPΔ2 can tolerate insertion of a quite large polypeptide (around 241 aa) without any negative impact on its cell entry ability. This is very important since the bigger the immunogens is, the stronger and more efficient the immune responses will be, in general.

The following question is whether insertion of v3-v5 large polypeptide in EboGP would change the EboGP-fusion protein to be able to infect CD4+ T cells, since this polypeptide contains CD4 and co-receptor binding sites. It is known that CD4+ T cells (C8166 T cells) are resistant to EboGP-mediated virus entry (FIG. 5B; (44)). Hence, we use each LVPs stock described above to infect T lymphoid cell line (C8166 T cells). Results revealed that while HIV Env (T-tropic) incorporated LVPs were able to infect C8166 T cells efficiently, all EBoGPΔ2, EboGPΔ2/HIV-v3 and EBoGPΔ2/HIVv3-v5 pseudotyped LVPs could not mediate infection in C8166 T cells (FIG. 8D). These results clearly indicate that the replacement of the MLD in HIV V3-V5 large polypeptide in EboGP is able to increase virus entry in THP1, a human monocytic cell line, but had no infection ability for CD4+ T lymphocytes.

Example 5. Significantly Stronger Anti-HIV Env Immune Responses Induced by Virus-Like Particles Containing EbGPΔ2/HIVv3 Chimeric Protein Since EbGPΔ2/HIVv3-pseudotyping HIV VLPs was able to mediate significantly virus entry towards MDDCs/MDMs, we next investigated whether the incorporation of EbGPΔ2/HIVv3 and EbGPΔ2/HIVv3-5 into HIV VLPs could induce immunogenicity of HIV VLPs in vivo. As depicted in FIG. 9D-F, we first immunized BALB/C mice with 100 ng of HIVEnv(M) or EboGPΔM/V3-pseudotyped HIV VLPs on days 0, and 21. At day 28 of post-immunization, the mice sera were collected, and measured for anti-HIVgp120, and -p24 antibody levels by corresponding ELISA. Results revealed that HIV-specific humeral immune responses against HIV Envgp120 and Gagp24 titers for mice immunized with EboGPΔM/V3-pseudotyped VLPs were significantly higher than that with HIVgp(M)-VLPs (FIGS. 9E and F), while EboGPΔM/V3-5-pseudotyped HIV VLPs immunization induced similar levels compared to HIVgp (M)-VLPs (FIG. 9E an F).

Example 6. rVSV Expressing EbGPΔ2/HIVv3 Chimeric Protein Induced Significantly Stronger Robust Anti-HIV Env Immune Responses We further tested whether the co-expression of EbGPΔ2/HIVv3 and HIV Env glycoprotein in recombinant vesicular stomatitis virus (rVSV) vector can also induce robust host immune responses in vivo. To do so, different VSV vector, including rVSV co-expressing HIV envelop glycoprotein and VSVG (rVSV-HIVEnv/VSVG, FIG. 10Aa), rVSV co-expressing HIV envelop glycoprotein and the wild type EboGPwt (rVSV-HIVEnv/EboGPwt, FIG. 10Ab) or rVSV co-expressing HIV envelop glycoprotein and EboGPΔM/V3 (rVSV-HIVEnv/EboGPΔM/V3, FIG. 10Ac) was rescued in VeroE6 by using a reverse genetics technology (1), and used to immunize the BALB/c mice. Briefly, each rVSV stock was produced in VeroE6 cells and concentrated by ultracentrifugation, and virus titers were titrated in Vero E6 cells. Then, the BALB/c mice were injected subcutaneously with 1×106 TCID50 of each of rVSV-HIVEnv/VSVG, rVSV-HIVEnv/EboGPwt, or rVSV-HIVEnv/EboGPΔM/V3, as indicated. At 35 days post-immunization, the sera from immunized mice were collected and measured for the anti-HIVgp120 antibody levels with anti-HIVgp120 ELISAs.

Results have shown that when this EboGPDM/V3 fusion protein was co-expressed with HIV Env glycoproteins in rVSV vector, it elicited more robust anti-HIV antibody responses than other rVSV vectors co-expressing either HIVEnv/VSVG or HIVEnv/EboGPwt (FIG. 100).

The scope of the claims should not be limited by the preferred embodiments set forth in the examples but should be given the broadest interpretation consistent with the description as a whole.

REFERENCES

1. Agnandji, S. T., A. Huttner, M. E. Zinser, P. Njuguna, C. Dahlke, J. F. Fernandes, S. Yerly, J. A. Dayer, V. Kraehling, R. Kasonta, A. A. Adegnika, M. Altfeld, F. Auderset, E. B. Bache, N. Biedenkopf, S. Borregaard, J. S. Brosnahan, R. Burrow, C. Combescure, J. Desmeules, M. Eickmann, S. K. Fehling, A. Finckh, A. R. Goncalves, M. P. Grobusch, J. Hooper, A. Jambrecina, A. L. Kabwende, G. Kaya, D. Kimani, B. Lell, B. Lemaitre, A. W. Lohse, M. Massinga-Loembe, A. Matthey, B. Mordmuller, A. Nolting, C. Ogwang, M. Ramharter, J. Schmidt-Chanasit, S. Schmiedel, P. Silvera, F. R. Stahl, H. M. Staines, T. Strecker, H. C. Stubbe, B. Tsofa, S. Zaki, P. Fast, V. Moorthy, L. Kaiser, S. Krishna, S. Becker, M. P. Kieny, P. Bejon, P. G. Kremsner, M. M. Addo, and C. A. Siegrist. 2016. Phase 1 Trials of rVSV Ebola Vaccine in Africa and Europe. The New England journal of medicine 374:1647-1660.
2. Ao, Z., J. Huang, X. Tan, X. Wang, T. Tian, X. Zhang, Q. Ouyang, and X. Yao. 2016. Characterization of the single cycle replication of HIV-1 expressing *Gaussia* luciferase in human PBMCs, macrophages, and in CD4(+) T cell-grafted nude mouse. Journal of virological methods 228: 95-102.
3. Berges, C., C. Naujokat, S. Tinapp, H. Wieczorek, A. Hoh, M. Sadeghi, G. Opelz, and V. Daniel. 2005. A cell line model for the differentiation of human dendritic cells. Biochemical and biophysical research communications 333:896-907.
4. Bosio, C. M., B. D. Moore, K. L. Warfield, G. Ruthel, M. Mohamadzadeh, M. J. Aman, and S. Bavari. 2004. Ebola and Marburg virus-like particles activate human myeloid dendritic cells. Virology 326:280-287.
5. Choi, J. H., and M. A. Croyle. 2013. Emerging targets and novol approaches to Ebola virus prophylaxis and treatment. BioDrugs 27:565-583.
6. Dai, L., J. Song, X. Lu, Y. Q. Deng, A. M. Musyoki, H. Cheng, Y. Zhang, Y. Yuan, H. Song, J. Haywood, H. Xiao, J. Yan, Y. Shi, C. F. Qin, J. Qi, and G. F. Gao. 2016. Structures of the Zika Virus Envelope Protein and Its Complex with a Flavivirus Broadly Protective Antibody. Cell host & microbe 19:696-704.
7. Demberg, T., and M. Robert-Guroff. 2012. Controlling the HIV/AIDS epidemic: current status and global challenges. Front Immunol 3:250.
8. Deruaz, M., B. Moldt, K. M. Le, K. A. Power, V. D. Vrbanac, S. Tanno, M. S. Ghebremichael, T. M. Allen, A. M. Tager, D. R. Burton, and A. D. Luster. 2016. Protection of Humanized Mice From Repeated Intravaginal HIV Challenge by Passive Immunization: A Model for Studying the Efficacy of Neutralizing Antibodies In Vivo. The Journal of infectious diseases 214:612-616.
9. Engelmayer, J., M. Larsson, A. Lee, M. Lee, W. I. Cox, R. M. Steinman, and N. Bhardwaj. 2001. Mature dendritic cells infected with canarypox virus elicit strong anti-human immunodeficiency virus CD8+ and CD4+ T-cell responses from chronically infected individuals. Journal of virology 75:2142-2153.
10. Fuchs, J. D., I. Frank, M. L. Elizaga, M. Allen, N. Frahm, N. Kochar, S. Li, S. Edupuganti, S. A. Kalams, G. D. Tomaras, R. Sheets, M. Pensiero, M. A. Tremblay, T. J. Higgins, T. Latham, M. A. Egan, D. K. Clarke, J. H. Eldridge, H. S. Group, A. the National Institutes of, H. I. V. V. T. N. Infectious Diseases, M. Mulligan, N. Rouphael, S. Estep, K. Rybczyk, D. Dunbar, S. Buchbinder, T. Wagner, R. Isbell, V. Chinnell, J. Bae, G. Escamilla, J. Tseng, R. Fair, S. Ramirez, G. Broder, L. Briesemeister, and A. Ferrara. 2015. First-in-Human Evaluation of the Safety and Immunogenicity of a Recombinant Vesicular Stomatitis Virus Human Immunodeficiency Virus-1 gag Vaccine (HVTN 090). Open forum infectious diseases 2:ofv082.
11. Geisbert, T. W., A. C. Lee, M. Robbins, J. B. Geisbert, A. N. Honko, V. Sood, J. C. Johnson, S. de Jong, I. Tavakoli, A. Judge, L. E. Hensley, and I. Maclachlan. 2010. Postexposure protection of non-human primates against a lethal Ebola virus challenge with RNA interference: a proof-of-concept study. Lancet 375:1896-1905.
12. Hawiger, D., K. Inaba, Y. Dorsett, M. Guo, K. Mahnke, M. Rivera, J. V. Ravetch, R. M. Steinman, and M. C. Nussenzweig. 2001. Dendritic cells induce peripheral T cell unresponsiveness under steady state conditions in vivo. The Journal of experimental medicine 194:769-779.
13. Haynes, B. F., P. B. Gilbert, M. J. McElrath, S. Zolla-Pazner, G. D. Tomaras, S. M. Alam, D. T. Evans, D. C. Montefiori, C. Karnasuta, R. Sutthent, H. X. Liao, A. L. DeVico, G. K. Lewis, C. Williams, A. Pinter, Y. Fong, H. Janes, A. DeCamp, Y. Huang, M. Rao, E. Billings, N. Karasavvas, M. L. Robb, V. Ngauy, M. S. de Souza, R. Paris, G. Ferrari, R. T. Bailer, K. A. Soderberg, C. Andrews, P. W. Berman, N. Frahm, S. C. De Rosa, M. D. Alpert, N. L. Yates, X. Shen, R. A. Koup, P. Pitisuttithum, J. Kaewkungwal, S. Nitayaphan, S. Rerks-Ngarm, N. L. Michael, and J. H. Kim. 2012. Immune-correlates analysis of an HIV-1 vaccine efficacy trial. The New England journal of medicine 366:1275-1286.
14. Henao-Restrepo, A. M., A. Camacho, I. M. Longini, C. H. Watson, W. J. Edmunds, M. Egger, M. W. Carroll, N. E. Dean, I. Diatta, M. Doumbia, B. Draguez, S. Duraffour, G. Enwere, R. Grais, S. Gunther, P. S. Gsell, S. Hossmann, S. V. Watle, M. K. Konde, S. Keita, S. Kone, E. Kuisma, M. M. Levine, S. Mandal, T. Mauget, G. Norheim, X. Riveros, A. Soumah, S. Trelle, A. S. Vicari, J. A. Rottingen, and M. P. Kieny. 2017. Efficacy and effectiveness of an rVSV-vectored vaccine in preventing Ebola virus disease: final results from the Guinea ring vaccination, open-label, cluster-randomised trial (Ebola Ca Suffit!). Lancet 389:505-518.
15. Ho, D. H., A. U. Neumann, A. P. Perelson, W. Chen, J. M. Leonard, and M. Markowitz. 1995. Rapid turnover of plasma virions and CD4 lymphocytes in HIV-1 infection. Nat. Med. 373:123-126.
16. Hoffmann, M., M. Gonzalez Hernandez, E. Berger, A. Marzi, and S. Pohlmann. 2016. The Glycoproteins of All Filovirus Species Use the Same Host Factors for Entry into Bat and Human Cells but Entry Efficiency Is Species Dependent. PLoS one 11:e0149651.
17. Huttner, A., J. A. Dayer, S. Yerly, C. Combescure, F. Auderset, J. Desmeules, M. Eickmann, A. Finckh, A. R. Goncalves, J. W. Hooper, G. Kaya, V. Krahling, S. Kwilas, B. Lemaitre, A. Matthey, P. Silvera, S. Becker, P. E. Fast, V. Moorthy, M. P. Kieny, L. Kaiser, C. A. Siegrist, and V. S.-E. Consortium. 2015. The effect of dose on the safety and immunogenicity of the VSV Ebola candidate vaccine: a randomised double-blind, placebo-controlled phase 1/2 trial. The Lancet. Infectious diseases 15:1156-1166.
18. Ibeh, N., J. C. Nshogozabahizi, and S. Aris-Brosou. 2016. Both Epistasis and Diversifying Selection Drive the Structural Evolution of the Ebola Virus Glycoprotein Mucin-Like Domain. Journal of virology 90:5475-5484.
19. Kaletsky, R. L., G. Simmons, and P. Bates. 2007. Proteolysis of the Ebola virus glycoproteins enhances virus binding and infectivity. Journal of virology 81:13378-13384.
20. Laman, J. D., M. M. Schellekens, Y. H. Abacioglu, G. K. Lewis, M. Tersmette, R. A. Fouchier, J. P. Langedijk, E. Claassen, and W. J. Boersma. 1992. Variant-specific monoclonal and group-specific polyclonal human immunodeficiency virus type 1 neutralizing antibodies raised with synthetic peptides from the gp120 third variable domain. Journal of virology 66:1823-1831.
21. Lee, J. E., M. L. Fusco, A. J. Hessell, W. B. Oswald, D. R. Burton, and E. O. Saphire. 2008. Structure of the Ebola virus glycoprotein bound to an antibody from a human survivor. Nature 454:177-182.
22. Lennemann, N. J., B. A. Rhein, E. Ndungo, K. Chandran, X. Qiu, and W. Maury. 2014. Comprehensive functional analysis of N-linked glycans on Ebola virus GP1. mBio 5:e00862-00813.
23. Li, H., T. Ying, F. Yu, L. Lu, and S. Jiang. 2015. Development of therapeutics for treatment of Ebola virus infection, Microbes and infection 17:109-117.
24. Liu, J., K. Ghneim, D. Sok, W. J. Bosche, Y. Li, E. Chipriano, B. Berkemeier, K. Oswald, E. Borducchi, C. Cabral, L. Peter, A. Brinkman, M. Shetty, J. Jimenez, J. Mondesir, B. Lee, P. Giglio, A. Chandrashekar, P. Abbink, A. Colantonio, C. Gittens, C. Baker, W. Wagner, M. G. Lewis, W. Li, R. P. Sekaly, J. D. Lifson, D. R. Burton, and D. H. Barouch. 2016. Antibody-mediated protection against SHIV challenge includes systemic clearance of distal virus. Science 353:1045-1049.
25. Liu, Y. J. 2001. Dendritic cell subsets and lineages, and their functions in innate and adaptive immunity. Cell 106:259-262.
26. Martinez, O., J. C. Johnson, A. Honko, B. Yen, R. S. Shabman, L. E. Hensley, G. G. Olinger, and C. F. Basler. 2013. Ebola virus exploits a monocyte differentiation program to promote its entry. Journal of virology 87:3801-3814.
27. Martinez, O., L. W. Leung, and C. F. Basler. 2012. The role of antigen-presenting cells in filoviral hemorrhagic fever: gaps in current knowledge. Antiviral research 93:416-428.
28. Martinez, O., C. Valmas, and C. F. Basler. 2007. Ebola virus-like particle-induced activation of NF-kappaB and Erk signaling in human dendritic cells requires the glycoprotein mucin domain. Virology 364:342-354.
29. Marzi, A., P. Moller, S. L. Hanna, T. Harrer, J. Eisemann, A. Steinkasserer, S. Becker, F. Baribaud, and S. Pohlmann. 2007. Analysis of the interaction of Ebola virus glycoprotein with DC-SIGN (dendritic cell-specific intercellular adhesion molecule 3-grabbing nonintegrin) and its homologue DC-SIGNR. The Journal of infectious diseases 196 Suppl 2:S237-246.
30. Marzi, A., S. J. Robertson, E. Haddock, F. Feldmann, P. W. Hanley, D. P. Scott, J. E. Strong, G. Kobinger, S. M. Best, and H. Feldmann. 2015. EBOLA VACCINE. VSV-EBOV rapidly protects macaques against infection with the 2014/15 Ebola virus outbreak strain. Science 349:739-742.
31. Matsuno, K., E. Nakayama, O. Noyori, A. Marzi, H. Ebihara, T. Irimura, H. Feldmann, and A. Takada. 2010. C-type lectins do not act as functional receptors for filovirus entry into cells. Biochemical and biophysical research communications 403:144-148.
32. Medina, M. F., G. P. Kobinger, J. Rux, M. Gasmi, D. J. Looney, P. Bates, and J. M. Wilson. 2003. Lentiviral vectors pseudotyped with minimal filovirus envelopes increased gene transfer in murine lung. Molecular therapy: the journal of the American Society of Gene Therapy 8:777-789.
33. Misasi, J., M. S. Gilman, M. Kanekiyo, M. Gui, A. Cagigi, S. Mulangu, D. Corti, J. E. Ledgerwood, A. Lanzavecchia, J. Cunningham, J. J. Muyembe-Tamfun, U. Baxa, B. S. Graham, Y. Xiang, N. J. Sullivan, and J. S. McLellan. 2016. Structural and molecular basis for Ebola virus neutralization by protective human antibodies. Science 351:1343-1346.
34. Oestereich, L., A. Ludtke, S. Wurr, T. Rieger, C. Munoz-Fontela, and S. Gunther. 2014. Successful treatment of advanced Ebola virus infection with T-705 (favipiravir) in a small animal model. Antiviral Res 105:17-21.
35. Ofuji, K., Y. Tada, T. Yoshikawa, M. Shimomura, M. Yoshimura, K. Saito, Y. Nakamoto, and T. Nakatsura. 2015. A peptide antigen derived from EGFR T790M is immunogenic in nonsmall cell lung cancer. International journal of oncology 46:497-504.
36. Rerks-Ngarm, S., P. Pitisuttithum, S. Nitayaphan, J. Kaewkungwal, J. Chiu, R. Paris, N. Premsri, C. Namwat, M. de Souza, E. Adams, M. Benenson, S. Gurunathan, J. Tartaglia, J. G. McNeil, D. P. Francis, D. Stablein, D. L. Birx, S. Chunsuttiwat, C. Khamboonruang, P. Thongcharoen, M. L. Robb, N. L. Michael, P. Kunasol, J. H. Kim, and M.-T. Investigators. 2009. Vaccination with ALVAC and AIDSVAX to prevent HIV-1 infection in Thailand. The New England journal of medicine 361: 2209-2220.
37. Reynard, O., M. Borowiak, V. A. Volchkova, S. Delpeut, M. Mateo, and V. E. Volchkov. 2009. Ebolavirus glycoprotein GP masks both its own epitopes and the presence of cellular surface proteins. Journal of virology 83:9596-9601.
38. Richman, D. D. 1993. HIV drug resistance. Annu. Rev. Pharmacol. Toxicol. 33:149.
39. Schornberg, K., S. Matsuyama, K. Kabsch, S. Delos, A. Bouton, and J. White. 2006. Role of endosomal cathepsins in entry mediated by the Ebola virus glycoprotein. Journal of virology 80:4174-4178.
40. Tran, E. E., J. A. Simmons, A. Bartesaghi, C. J. Shoemaker, E. Nelson, J. M. White, and S. Subramaniam. 2014. Spatial localization of the Ebola virus glycoprotein mucin-like domain determined by cryo-electron tomography. Journal of virology 88:10958-10962.
41. von Wyl, V., S. Yerly, J. Boni, C. Shah, C. Cellerai, T. Klimkait, M. Battegay, E. Bernasconi, M. Cavassini, H. Furrer, B. Hirschel, P. L. Vernazza, B. Ledergerber, and H. F. Gunthard. 2011. Incidence of HIV-1 drug resistance among antiretroviral treatment-naive individuals starting modern therapy combinations. Clin Infect Dis 54:131-140.
42. Warren, T. K., J. Wells, R. G. Panchal, K. S. Stuthman, N. L. Garza, S. A. Van Tongeren, L. Dong, C. J. Retterer, B. P. Eaton, G. Pegoraro, S. Honnold, S. Bantia, P. Kotian, X. Chen, B. R. Taubenheim, L. S. Welch, D. M. Minning, Y. S. Babu, W. P. Sheridan, and S. Bavari. 2014. Protection against filovirus diseases by a novel broad-spectrum nucleoside analogue BCX4430. Nature 508:402-405.
43. Wei, X., S. K. Ghosh, M. E. Taylor, V. A. Johnson, E. A. Emini, P. Deutsh, J. D. Lifson, S. Bonhoeffer, M. A. Nowak, B. H. Hahn, M. S. Saag, and G. M. Shaw. 1995. Viral dynamics in human immunodeficiency virus type 1 infection. Nat. Med. 373:117-122.
44. Wilson, J. A., M. Hevey, R. Bakken, S. Guest, M. Bray, A. L. Schmaljohn, and M. K. Hart. 2000. Epitopes involved in antibody-mediated protection from Ebola virus. Science 287:1664-1666.
45. Zhang, X., Z. Ao, A. Bello, X. Ran, S. Liu, J. Wigle, G. Kobinger, and X. Yao. 2016. Characterization of the inhibitory effect of an extract of Prunella vulgaris on Ebola virus glycoprotein (GP)-mediated virus entry and infection. Antiviral research 127:20-31.
46. Zhao, H., E. Fernandez, K. A. Dowd, S. D. Speer, D. J. Platt, M. J. Gorman, J. Govero, C. A. Nelson, T. C. Pierson, M. S. Diamond, and D. H. Fremont. 2016. Structural Basis of Zika Virus-Specific Antibody Protection. Cell 166:1016-1027.
47. Witko, S. E. et al. An efficient helper-virus-free method for rescue of recombinant paramyxoviruses and rhadoviruses from a cell line suitable for vaccine development. Journal of virological methods 135, 91-101, doi:10.1016/j.jviromet.2006.02.006 (2006).

TABLE 1

Sequence of ESVGPopt-delta2
Table 1
Sequence of EBVGPopt-delta2

```
ATGGGTGTGACCGGT ATCCTGCAGCTGCCG CGTGATCGCTTCAAA CGTACCTCTTTCTTT CTGTGGGTTATCATC
 M  G  V  T  G   I  L  Q  L  P    R  D  R  F  K    R  T  S  F  F    L  W  V  I  I

CTGTTCCAGCGTACC TTTTCTATCCCGCTG GGTGTTATTCATAAC TCCACCCTGCAGGTG AGCGACGTTGATAAA
 L  F  Q  R  T   F  S  I  P  L    G  V  I  H  N    S  T  L  Q  V    S  D  V  D  K

CTGGTTTGCCGTGAC AAACTGTCTTCTACC AACCAGCTGCGCTCC GTGGGCCTGAACCTG GAAGGTAACGGTGTT
 L  V  C  R  D   K  L  S  S  T    N  Q  L  R  S    V  G  L  N  L    E  G  N  G  V

GCAACCGACGTGCCG TCTGCGACCAAACGC TGGGGTTTCCGCTCC GGTGTTCCGCCGAAA GTTGTTAACTACGAA
 A  T  D  V  P   S  A  T  K  R    W  G  F  R  S    G  V  P  P  K    V  V  N  Y  E

GCGGGCGAATGGGCT GAAAACTGTTATAAC CTGGAAATCAAGAAA CCGGACGGCTCCGAG TGCCTGCCGGCAGCT
 A  G  E  W  A   E  N  C  Y  N    L  E  I  K  K    P  D  G  S  E    C  L  P  A  A

CCGGACGGTATTCGC GGCTTTCCGCGCTGT CGTTACGTTCATAAA GTTAGCGGTACTGGT CCGTGCGCAGGTGAC
 P  D  G  I  R   G  F  P  R  C    R  Y  V  H  K    V  S  G  T  G    P  C  A  G  D

TTTGCTTTCCACAAA GAGGGCGCGTTTTTC CTGTATGACCGCCTG GCATCCACCGTTATT TACCGTGGCACCACC
 F  A  F  H  K   E  G  A  F  F    L  Y  D  R  L    A  S  T  V  I    Y  R  G  T  T

TTCGCGGAAGGCGTT GTGGCGTTCCTGATC CTGCCGCAGGCTAAG AAAGATTTCTTTAGC AGCCACCCGCTGCGC
 F  A  E  G  V   V  A  F  L  I    L  P  Q  A  K    K  D  F  F  S    S  H  P  L  R

GAGCCGGTTAACGCG ACTGAGGATCCGTCT TCTGGTTATTACTCC ACCACTATCCGTTAC CAGGCAACTGGTTTC
 E  P  V  N  A   T  E  D  P  S    S  G  Y  Y  S    T  T  I  R  Y    Q  A  T  G  F

GGTACCAACGAAACT GAATACCTGTTCGAA GTTGATAACCTGACC TACGTTCAGCTGGAA AGCCGCTTCACTCCG
 G  T  N  E  T   E  Y  L  F  E    V  D  N  L  T    Y  V  Q  L  E    S  R  F  T  P

CAGTTCCTGCTGCAG CTGAACGAAACCATC TACACCAGCGGTAAA CGTTCCAACACCACC GGCAAACTGATCTGG
 Q  F  L  L  Q   L  N  E  T  I    Y  T  S  G  K    R  S  N  T  T    G  K  L  T  W

AAAGTTAACCCGGAG ATCGATACCACTATT GGTGAGTGGGCGTTT TGGGAAACCAAGAAA AACCTGACCCGCAAA
 K  V  N  P  E   I  D  T  T  I    G  E  W  A  F    W  E  T  K  K    N  L  T  R  K

ATCCGTTCCGAGGAAGGA-------------
 I  R  S  E  E  G

-----------------------AACACC ATCGCAGGTGTTGCT GGTCTGATCACCGGC GGTCGTCGTACCCGC
-----------------  ----N  T    I  A  G  V  A    G  L  I  T  G    G  R  R  T  R

CGTGAAGCTATTGTT AACGCACAGCCGAAA TGTAACCCGAACCTG CACTACTGGACCACT CAGGATGAAGGCGCT
 R  E  A  I  V   N  A  Q  P  K    C  N  P  N  L    H  Y  W  T  T    Q  D  E  G  A

GCTATCGGCCTGGCA TGGATCCCGTACTTC GGTCCGGCGGCTGAA GGTATCTATATCGAA GGTCTGATGCACAAC
 A  I  G  L  A   W  I  P  Y  F    G  P  A  A  E    G  I  Y  I  E    G  L  M  H  N

CAGGATGGTCTGATT TGCGGTCTGCGTCAG CTGGCGAACGAAACC ACTCAGGCGCTGCAG CTGTTCCTGCGCGCA
 Q  D  G  L  I   C  G  L  R  Q    L  A  N  E  T    Q  A  L  Q    L  F  L  R  A

ACCACCGAGCTGCGT ACCTTCTCTATCCTG AACCGTAAGGCGATC GACTTTCTGCTGCAG CGTTGGGGTGGTACC
 T  T  E  L  R   T  F  S  I  L    N  R  K  A  I    D  F  L  L  Q    R  W  G  G  T

TGCCATATCCTGGGT CCGGACTGCTGTATC GAGCCGCATGATTGG ACTAAAAACATCACT GACAAAATCGACCAG
 C  H  I  L  G   P  D  C  C  I    E  P  H  D  W    T  K  N  I  T    D  K  I  D  Q
```

TABLE 1-continued

Sequence of ESVGPopt-delta2
Table 1
Sequence of EBVGPopt-delta2

```
ATCATTCACGACTTC GTTGACAAAACCCTG CCGGACCAGGGCGAT AACGACAACTGGTGG ACCGGCTGGCGTCAG
 I  I  H  D  F   V  D  K  T  L   P  D  Q  G  D   N  D  N  W  W   T  G  W  R  Q

TGGATTCCGGCAGGC ATCGGCGTTACCGGT GTTATTATTGCTGTG ATTGCACTGTTTTGC ATTTGCAAGTTCGTT
 W  I  P  A  D   I  G  V  T  G   V  I  I  A  V   I  A  L  F  C   I  C  K  F  V

TTCTGA
 F  *
```

TABLE 2

Sequence of inserted HIV glycoprotein V3 region

```
                TTCAATGGAACAGGA CCATGTACAAATGTC AGCACAGTACAATGT ACACATGGAATCAGG
                 F  N  G  T  G   P  C  T  N  V   S  T  V  Q  C   T  H  G  I  R

CCAGTAGTATCAACT CAACTGCTGTTAAAT GGCAGTCTAGCAGAA GAAGATGTAGTAATT AGATCTGCCAATTTC
 P  V  V  S  T   Q  L  L  L  N   G  S  L  A  E   E  D  V  V  I   R  S  A  N  F

ACAGACAATGCTAAA ACCATAATAGTACAG CTGAACACATCTGTA GAAATTAATTGTACA AGACCCAACAACAAT
 T  D  N  A  K   T  I  I  V  Q   L  N  T  S  V   E  I  N  C  T   R  P  N  N  N

ACAAGAAAAAGTATC CGTATCCAGAGGGGA CCAGGGAGAGCATTT GTTACAATAGGAAAA ATAGGAAATATGAGA
 T  R  K  S  I   R  I  Q  R  G   P  G  R  A  F   V  T  I  G  K   I  G  N  M  R

CAAGCACATTGTAAC ATTAGTAGAGCAAAA TGGAATGCCACTTTA AAACAGATAGCTAGC AAATTAAGAGAACAA
 Q  A  H  C  N   I  S  R  A  D   W  N  A  T  L   K  Q  I  A  S   K  L  R  E  Q

TTTGGAAATAATAAA ACAATAATCTTTAAG CAATCCTCAGGA
 F  G  N  N  K   T  I  I  F  K   Q  S  S  G
```

Total 134 aa

Sequence of inserted HIV glycoprotein V3-V5 region

```
                TTCAATGGAACAGGA CCATGTACAAATGTC AGCACAGTACAATGT ACACATGGAATCAGG
                 F  N  G  T  G   P  C  T  N  V   S  T  V  Q  C   T  H  G  I  R

CCAGTAGTATCAACT CAACTGCTGTTAAAT GGCAGTCTAGCAGAA GAAGATGTAGTAATT AGATCTGCCAATTTC
 P  V  V  S  T   Q  L  L  L  N   G  S  L  A  E   E  D  V  V  I   R  S  A  N  F

ACAGACAATGCTAAA ACCATAATAGTACAG CTGAACACATCTGTA GAAATTAATTGTACA AGACCCAACAACAAT
 T  D  N  A  K   T  I  I  V  Q   L  N  T  S  V   E  I  N  C  T   R  P  N  N  N

ACAAGAAAAAGTATC CGTATCCAGAGGGGA CCAGGGAGAGCATTT GTTACAATAGGAAAA ATAGGAAATATGAGA
 T  R  K  S  I   R  I  Q  R  G   P  G  R  A  F   V  T  I  G  K   I  G  N  M  R

CAAGCACATTGTAAC ATTAGTAGAGCAAAA TGGAATGCCACTTTA AAACAGATAGCTAGC AAATTAAGAGAACAA
 Q  A  H  C  N   I  S  R  A  K   W  N  A  T  L   K  Q  I  A  S   K  L  R  E  Q

TTTGGAAATAATAAA ACAATAATCTTTAAG CAATCCTCAGGAGGG GACCCAGAAATTGTA ACGCACAGTTTTAAT
 F  G  N  N  K   T  I  I  F  K   Q  S  S  G  G   D  P  E  I  V   T  H  S  F  N

TGTGGAGGGGAATTT TTCTACTGTAATTCA ACACAACTGTTTAAT AGTACTTGGTTTAAT AGTACTTGGAGTACT
 C  G  G  E  F   F  Y  C  N  S   T  Q  L  F  N   S  T  W  F  N   S  T  W  S  T

GAAGGGTCAAATAAC ACTGAAGGAAGTGAC ACAATCACACTCCCA TGCAGAATAAAACAA TTTATAAACATGTGG
 E  G  S  N  N   T  E  G  S  D   T  I  T  L  P   C  R  I  K  Q   F  I  N  M  W

CAGGAAGTAGGAAAA GCAATGTATGCCCCT CCCATCAGTGGACAA ATTAGATGTTCATCA AATATTACTGGGCTG
 Q  E  V  G  K   A  M  Y  A  P   P  I  S  G  Q   I  R  C  S  S   N  I  T  G  L

CTATTAACAAGAGAT GGTGGTAATAACAAC AATGGGTCCGAGATC TTCAGACCTGGAGGA GGC
 L  L  T  R  D   G  G  N  N  N   N  G  S  E  I   F  R  P  G  G   G
```

Total 241 aa

Sequence of inserted ZiKa glycoprotein DIII (LR) domain

```
                                           GTGTCA TACTCACTGTGCACT GCAGCATTCACATTC ACCAAGGTGCCAGCT
                                            V  S   Y  S  L  C  T   A  A  F  T  F   T  K  V  P  A
```

TABLE 2-continued

```
GAGACACTGCACGGT ACTGTGACAGTGGAA GTGCAGTACGCTGGT ACCGACGGTCCTTGC AAGATCCCAGTGCAG
 E  T  L  H  G   T  V  T  V  E   V  Q  Y  A  G   T  D  G  P  C   K  I  P  V  Q

ATGGCAGTAGACATG CAGACTCTGACTCCA GTGGGACGACTGATC ACTGCTAACCCTGTG ATCACTGAGTCAACT
 M  A  V  D  M   Q  T  L  T  P   V  G  R  L  I   T  A  N  P  V   I  T  E  S  T

GAGAACTCCAAGATG ATGCTGGAACTGGAC CCACCATTCGGAGAC TCCTACATCGTGATC GGCGTGGGTGACAAG
 E  N  S  K  M   M  L  E  L  D   P  P  F  G  D   S  Y  I  V  I   G  V  G  D  K

AAGATCACCCATCAC TGGCATCGATCCGGC
 K  I  T  H  H   W  H  R  S  G

Total 102 aa
```

TABLE 3

Sequence of Marburg virus glycoprotein (mucin like domain deleted)

MABV GP (MLD indicated)
Atgaagactacatgtatatttcggtcttatcttgatccaaaggataaa aactcttcctatttagagatagctagtaacaaccaaccccaaaatatgg attcggtatgctccggaactctccagaagacagaagatgtccatctgatg ggattcacactgagtgggcaaaaagttgctgattccccttggaggcatc caagcgatgggctttcaggacaggtgtacctcccaagaatgttgagtata cagaaggggaggaagccaaaacatgctacaatataagtgtaacggatccc tctggaaaatccttgctgttggatcctcctaccaacatccgtgactatcc taaatgcaaaactatccatcatattcaaggtcaaaaccctcatgcgcaag ggatcgccctccatctgtggggagcattttcctgtatgatcgcattgcc tccacaacaatgtaccgaggcagagtcttcactgaagggaacatagcagc tatgattgtcaataagacagtgcacaaaatgattttctcgaggcaaggac aagggtaccgtcacatgaatctgacttctactaataaatattggacaagt aacaacggaacacaaacgaatgacactggatgcttcggcgctcttcaaga atacaactccacgaagaatcaaacatgtgctccgtccaaaatacattcac cactgcccacaacccgctcagagattaaacccacaagcaccccaactgat gccaccgcactcaacaccaca---

--Mucin deletion ---------

TABLE 3-continued

Sequence of Marburg virus glycoprotein (mucin like domain deleted)

caacatcttgtatatttcagaaagaaacgaagtatcctctggagggaagg cgacatgttcccttttctggacgggttaataaatgctccaattgattttg atccagttccaaatacaaagacgatctttgatgaatcttctagttctggt gcttcggctgaggaagatcaacatgcctccccaatatcagtttaactttt atcctattttcctaatataaatgaaaacactgcctactctggagaaaatg agaacgattgtgatgcagagttaagaatttggagcgttcaggaggatgac ctggcagcagggctcagttggataccgttttttggccctggaatcgaagg actttatactgctggtttaattaaaaaccaaaacaatttggtatgcaggt tgaggcgtctagccaatcaaactgccaaatccttggaactcttattaaga gtcacaaccgaggagaggacattttccttaattaatagacatgccattga ttttctactcacaagtgagaggaacatgcaaagtgcttggacctgatt gttgcatcggaatagaagacttgtccaggaatatttcagagcaaattgac caaatcaaaaaagatgaacaaaagagggactggttggggtataggtgg taaatggtggacatccgactggggtgttcttactaacttgggcattttgc tactattatccatagctgtcttgattgctctatcctgtatttgtcgtatc tttaccaaatatatcgggtaa

The invention claimed is:

1. A method of targeting a peptide of interest to an antigen presenting cell comprising:
   providing a virus-like particle comprising as glycoprotein a Filoviridae Virus chimeric glycoprotein fusion protein comprising an antigenic protein of interest inserted in the mucin-like domain of the Filoviridae Virus glycoprotein such that the antigenic peptide of interest is expressed at apex and sides of the chimeric glycoprotein fusion protein; and
   immunizing an individual in need of immunization against the antigenic peptide of interest with an effective amount of the virus-like particle, wherein expression of the antigenic peptide of interest at the apex and the sides of the chimeric glycoprotein fusion protein exposes the antigenic peptide of interest to the individual's immune system.

2. The method according to claim 1 wherein the Filoviridae Virus is Ebola Virus or Marburg Virus.

3. The method according to claim 1 wherein the mucin-like domain comprises amino acids 305-501 of the Ebola Virus glycoprotein.

4. The method according to claim 1 wherein the mucin-like domain comprises amino acids 257-501 of Marburg virus glycoprotein.

5. The method according to claim 1 wherein the mucin-like domain is a tolerated deletion of native mucin-like domain.

6. The method according to claim 1 further comprising an HIV glycoprotein V3 and/or V3-V5 domain.

7. A method of eliciting an enhanced immune response against a peptide of interest comprising:

provi ding a virus-like particle comprising as glycoprotein a Filoviridae Virus chimeric glycoprotein fusion protein comprising an antigenic protein of interest inserted in the mucin-like domain of the Filoviridae Virus glycoprotein such that the antigenic peptide of interest is expressed at apex and sides of the chimeric glycoprotein fusion protein; and immunizing an individual in need of immunization against the antigenic peptide of interest with an effective amount of the virus-like particle, wherein expression of the antigenic peptide of interest at the apex and the sides of the chimeric glycoprotein fusion protein exposes the antigenic peptide of interest to the individual's immune system.

8. The method according to claim 7 wherein the mucin-like domain comprises amino acids 305-501 of the Ebola Virus glycoprotein.

9. The method according to claim 7 wherein the mucin-like domain comprises amino acids 257-501 of Marburg virus glycoprotein.

10. The method according to claim 7 wherein the mucin-like domain is a tolerated deletion of native mucin-like domain.

11. The method according to claim 7 further comprising an HIV glycoprotein V3 domain.

12. The method according to claim 1 wherein the antigenic peptide of interest is a heterologous peptide.

13. The method according to claim 7 wherein the antigenic peptide of interest is a heterologous peptide.

* * * * *

SEQUENCE LISTING

<160> NUMBER OF SEQ ID NOS: 9

<210> SEQ ID NO 1
<211> LENGTH: 1500
<212> TYPE: DNA
<213> ORGANISM: Ebola virus
<220> FEATURE:
<221> NAME/KEY: misc_feature
<222> LOCATION: (918)..(919)
<223> OTHER INFORMATION: Deletion of mucin like domain

<400> SEQUENCE: 1
atgggtgtga ccggtatcct gcagctgccg cgtgatcgct tcaaacgtac ctctttcttt     60
ctgtgggtta tcatcctgtt ccagcgtacc ttttctatcc cgctgggtgt tattcataac    120 tccacccctgc aggtgagcga cgttgataaa ctggtttgcc gtgacaaact gtcttctacc    180
```

-continued

```
aaccagctgc gctccgtggg cctgaacctg gaaggtaacg gtgttgcaac cgacgtgccg     240
tctgcgacca aacgctgggg tttccgctcc ggtgttccgc cgaaagttgt taactacgaa     300
gcgggcgaat gggctgaaaa ctgttataac ctggaaatca agaaaccgga cggctccgag     360
tgcctgccgg cagctccgga cggtattcgc ggctttccgc gctgtcgtta cgttcataaa     420
gttagcggta ctggtccgtg cgcaggtgac tttgcttttc caaagagggc gcgttttttc     480
ctgtatgacc gcctggcatc caccgttatt accgtggca ccaccttcgc ggaaggcgtt     540
gtggcgttcc tgatcctgcc gcaggctaag aaagatttct ttagcagcca cccgctgcgc     600
gagccggtta acgcgactga ggatccgtct tctggttatt actccaccac tatccgttac     660
caggcaactg gtttcggtac aacgaaact gaatacctgt tcgaagttga taacctgacc     720
tacgttcagc tggaaagccg cttcactccg cagttcctgc tgcagctgaa cgaaaccatc     780
tacaccagcg gtaaacgttc caacaccacc ggcaaactga tctggaaagt taacccggag     840
atcgatacca ctattggtga gtgggcgttt tgggaaacca agaaaaacct gacccgcaaa     900
atccgttccg aggaaggaaa caccatcgca ggtgttgctg gtctgatcac cggcggtcgt     960
cgtacccgcc gtgaagctat tgttaacgca cagccgaaat gtaacccgaa cctgcactac    1020
tggaccactc aggatgaagg cgctgctatc ggcctggcat ggatcccgta cttcggtccg    1080
gcggctgaag gtatctatat cgaaggtctg atgcacaacc aggatggtct gatttgcggt    1140
ctgcgtcagc tggcgaacga aaccactcag gcgctgcagc tgttcctgcg cgcaaccacc    1200
gagctgcgta ccttctctat cctgaaccgt aaggcgatcg actttctgct gcagcgttgg    1260
ggtggtacct gccatatcct gggtccggac tgctgtatcg agccgcatga ttggactaaa    1320
aacatcactg acaaaatcga ccagatcatt cacgacttcg ttgacaaaac cctgccggac    1380
cagggcgata cgacaactg gtggaccggc tggcgtcagt ggattccggc aggcatcggc    1440
gttaccggtg ttattattgc tgtgattgca ctgttttgca tttgcaagtt cgttttctga    1500
```

<210> SEQ ID NO 2
<211> LENGTH: 499
<212> TYPE: PRT
<213> ORGANISM: ebola virus

<400> SEQUENCE: 2

```
Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140
```

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
            165                 170                 175

Ala Glu Gly Val Val Ala Phe Leu Ile Leu Pro Gln Ala Lys Lys Asp
        180                 185                 190

Phe Phe Ser Ser His Pro Leu Arg Glu Pro Val Asn Ala Thr Glu Asp
    195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
            245                 250                 255

Asn Glu Thr Ile Tyr Thr Ser Gly Lys Arg Ser Asn Thr Thr Gly Lys
        260                 265                 270

Leu Ile Trp Lys Val Asn Pro Glu Ile Asp Thr Thr Ile Gly Glu Trp
    275                 280                 285

Ala Phe Trp Glu Thr Lys Lys Asn Leu Thr Arg Lys Ile Arg Ser Glu
290                 295                 300

Glu Gly Asn Thr Ile Ala Gly Val Ala Gly Leu Ile Thr Gly Gly Arg
305                 310                 315                 320

Arg Thr Arg Arg Glu Ala Ile Val Asn Ala Gln Pro Lys Cys Asn Pro
            325                 330                 335

Asn Leu His Tyr Trp Thr Thr Gln Asp Glu Gly Ala Ala Ile Gly Leu
        340                 345                 350

Ala Trp Ile Pro Tyr Phe Gly Pro Ala Ala Glu Gly Ile Tyr Ile Glu
    355                 360                 365

Gly Leu Met His Asn Gln Asp Gly Leu Ile Cys Gly Leu Arg Gln Leu
370                 375                 380

Ala Asn Glu Thr Thr Gln Ala Leu Gln Leu Phe Leu Arg Ala Thr Thr
385                 390                 395                 400

Glu Leu Arg Thr Phe Ser Ile Leu Asn Arg Lys Ala Ile Asp Phe Leu
            405                 410                 415

Leu Gln Arg Trp Gly Gly Thr Cys His Ile Leu Gly Pro Asp Cys Cys
        420                 425                 430

Ile Glu Pro His Asp Trp Thr Lys Asn Ile Thr Asp Lys Ile Asp Gln
    435                 440                 445

Ile Ile His Asp Phe Val Asp Lys Thr Leu Pro Asp Gln Gly Asp Asn
450                 455                 460

Asp Asn Trp Trp Thr Gly Trp Arg Gln Trp Ile Pro Ala Gly Ile Gly
465                 470                 475                 480

Val Thr Gly Val Ile Ile Ala Val Ile Ala Leu Phe Cys Ile Cys Lys
            485                 490                 495

Phe Val Phe

<210> SEQ ID NO 3
<211> LENGTH: 402
<212> TYPE: DNA
<213> ORGANISM: Human immunodeficiency virus

<400> SEQUENCE: 3
ttcaatggaa caggaccatg tacaaatgtc agcacagtac aatgtacaca tggaatcagg    60

```
ccagtagtat caactcaact gctgttaaat ggcagtctag cagaagaaga tgtagtaatt    120
agatctgcca atttcacaga caatgctaaa accataatag tacagctgaa cacatctgta    180
gaaattaatt gtacaagacc caacaacaat acaagaaaaa gtatccgtat ccagagggga    240
ccagggagag catttgttac aataggaaaa ataggaaata tgagacaagc acattgtaac    300
attagtagag caaatggaa tgccacttta aaacagatag ctagcaaatt aagagaacaa    360
tttggaaata taaaacaat aatctttaag caatcctcag ga                        402
```

<210> SEQ ID NO 4
<211> LENGTH: 134
<212> TYPE: PRT
<213> ORGANISM: Human immunodeficiency virus

<400> SEQUENCE: 4

```
Phe Asn Gly Thr Gly Pro Cys Thr Asn Val Ser Thr Val Gln Cys Thr
1               5                   10                  15

His Gly Ile Arg Pro Val Val Ser Thr Gln Leu Leu Leu Asn Gly Ser
            20                  25                  30

Leu Ala Glu Glu Asp Val Val Ile Arg Ser Ala Asn Phe Thr Asp Asn
        35                  40                  45

Ala Lys Thr Ile Ile Val Gln Leu Asn Thr Ser Val Glu Ile Asn Cys
    50                  55                  60

Thr Arg Pro Asn Asn Thr Arg Lys Ser Ile Arg Ile Gln Arg Gly
65                  70                  75                  80

Pro Gly Arg Ala Phe Val Thr Ile Gly Lys Ile Gly Asn Met Arg Gln
                85                  90                  95

Ala His Cys Asn Ile Ser Arg Ala Lys Trp Asn Ala Thr Leu Lys Gln
            100                 105                 110

Ile Ala Ser Lys Leu Arg Glu Gln Phe Gly Asn Asn Lys Thr Ile Ile
        115                 120                 125

Phe Lys Gln Ser Ser Gly
    130
```

<210> SEQ ID NO 5
<211> LENGTH: 723
<212> TYPE: DNA
<213> ORGANISM: Human immunodeficiency virus

<400> SEQUENCE: 5

```
ttcaatggaa caggaccatg tacaaatgtc agcacagtac aatgtacaca tggaatcagg    60
ccagtagtat caactcaact gctgttaaat ggcagtctag cagaagaaga tgtagtaatt   120
agatctgcca atttcacaga caatgctaaa accataatag tacagctgaa cacatctgta   180
gaaattaatt gtacaagacc caacaacaat acaagaaaaa gtatccgtat ccagagggga   240
ccagggagag catttgttac aataggaaaa ataggaaata tgagacaagc acattgtaac   300
attagtagag caaatggaa tgccacttta aaacagatag ctagcaaatt aagagaacaa   360
tttggaaata taaaacaat aatctttaag caatcctcag gaggggaccc agaaattgta   420
acgcacagtt ttaattgtgg aggggaattt ttctactgta attcaacaca actgtttaat   480
agtacttggt ttaatagtac ttggagtact gaagggtcaa ataacactga aggaagtgac   540
acaatcacac tcccatgcag aataaaacaa tttataaaca tgtggcagga agtaggaaaa   600
gcaatgtatg cccctcccat cagtggacaa attagatgtt catcaaatat tactgggctg   660
ctattaacaa gagatggtgg taataacaac aatgggtccg agatcttcag acctggagga   720
``` ggc                                                                                     723

<210> SEQ ID NO 6
<211> LENGTH: 241
<212> TYPE: PRT
<213> ORGANISM: Human immunodeficiency virus

<400> SEQUENCE: 6

Phe Asn Gly Thr Gly Pro Cys Thr Asn Val Ser Thr Val Gln Cys Thr
1               5                   10                  15

His Gly Ile Arg Pro Val Val Ser Thr Gln Leu Leu Leu Asn Gly Ser
            20                  25                  30

Leu Ala Glu Glu Asp Val Val Ile Arg Ser Ala Asn Phe Thr Asp Asn
        35                  40                  45

Ala Lys Thr Ile Ile Val Gln Leu Asn Thr Ser Val Glu Ile Asn Cys
    50                  55                  60

Thr Arg Pro Asn Asn Asn Thr Arg Lys Ser Ile Arg Ile Gln Arg Gly
65                  70                  75                  80

Pro Gly Arg Ala Phe Val Thr Ile Gly Lys Ile Gly Asn Met Arg Gln
                85                  90                  95

Ala His Cys Asn Ile Ser Arg Ala Lys Trp Asn Ala Thr Leu Lys Gln
            100                 105                 110

Ile Ala Ser Lys Leu Arg Glu Gln Phe Gly Asn Asn Lys Thr Ile Ile
        115                 120                 125

Phe Lys Gln Ser Ser Gly Gly Asp Pro Glu Ile Val Thr His Ser Phe
    130                 135                 140

Asn Cys Gly Gly Glu Phe Phe Tyr Cys Asn Ser Thr Gln Leu Phe Asn
145                 150                 155                 160

Ser Thr Trp Phe Asn Ser Thr Trp Ser Thr Glu Gly Ser Asn Asn Thr
                165                 170                 175

Glu Gly Ser Asp Thr Ile Thr Leu Pro Cys Arg Ile Lys Gln Phe Ile
            180                 185                 190

Asn Met Trp Gln Glu Val Gly Lys Ala Met Tyr Ala Pro Pro Ile Ser
        195                 200                 205

Gly Gln Ile Arg Cys Ser Ser Asn Ile Thr Gly Leu Leu Leu Thr Arg
    210                 215                 220

Asp Gly Gly Asn Asn Asn Gly Ser Glu Ile Phe Arg Pro Gly Gly
225                 230                 235                 240

Gly

<210> SEQ ID NO 7
<211> LENGTH: 306
<212> TYPE: PRT
<213> ORGANISM: Zika Virus

<400> SEQUENCE: 7

Gly Thr Gly Thr Cys Ala Thr Ala Cys Thr Cys Ala Cys Thr Gly Thr
1               5                   10                  15

Gly Cys Ala Cys Thr Gly Cys Ala Gly Cys Ala Thr Thr Cys Ala Cys
            20                  25                  30

Ala Thr Thr Cys Ala Cys Cys Ala Ala Gly Gly Thr Gly Cys Cys Ala
        35                  40                  45

Gly Cys Thr Gly Ala Gly Ala Cys Ala Cys Thr Gly Cys Ala Cys Gly
    50                  55                  60

Gly Thr Ala Cys Thr Gly Thr Gly Ala Cys Ala Gly Thr Gly Gly Ala
65                  70                  75                  80

Ala Gly Thr Gly Cys Ala Gly Thr Ala Cys Gly Cys Gly Gly Thr
            85                  90                  95

Ala Cys Cys Gly Ala Cys Gly Gly Thr Cys Cys Thr Thr Gly Cys Ala
            100                 105                 110

Ala Gly Ala Thr Cys Cys Ala Gly Thr Gly Cys Ala Gly Ala Thr
            115                 120                 125

Gly Gly Cys Ala Gly Thr Ala Gly Ala Cys Ala Thr Gly Cys Ala Gly
        130                 135                 140

Ala Cys Thr Cys Thr Gly Ala Cys Thr Cys Cys Ala Gly Thr Gly Gly
145                 150                 155                 160

Gly Ala Cys Gly Ala Cys Thr Gly Ala Thr Cys Ala Cys Thr Gly Cys
            165                 170                 175

Thr Ala Ala Cys Cys Cys Thr Gly Thr Gly Ala Thr Cys Ala Cys Thr
        180                 185                 190

Gly Ala Gly Thr Cys Ala Ala Cys Thr Gly Ala Gly Ala Ala Cys Thr
            195                 200                 205

Cys Cys Ala Ala Gly Ala Thr Gly Ala Thr Gly Cys Thr Gly Gly Ala
        210                 215                 220

Ala Cys Thr Gly Gly Ala Cys Cys Cys Ala Cys Cys Ala Thr Thr Cys
225                 230                 235                 240

Gly Gly Ala Gly Ala Cys Thr Cys Cys Thr Ala Cys Ala Thr Cys Gly
            245                 250                 255

Thr Gly Ala Thr Cys Gly Gly Cys Gly Thr Gly Gly Gly Thr Gly Ala
            260                 265                 270

Cys Ala Ala Gly Ala Ala Gly Ala Thr Cys Ala Cys Cys Ala Thr
        275                 280                 285

Cys Ala Cys Thr Gly Gly Cys Ala Thr Cys Gly Ala Thr Cys Cys Gly
        290                 295                 300

Gly Cys
305

<210> SEQ ID NO 8
<211> LENGTH: 102
<212> TYPE: PRT
<213> ORGANISM: Zika virus

<400> SEQUENCE: 8

Val Ser Tyr Ser Leu Cys Thr Ala Ala Phe Thr Phe Thr Lys Val Pro
1               5                   10                  15

Ala Glu Thr Leu His Gly Thr Val Thr Val Glu Val Gln Tyr Ala Gly
            20                  25                  30

Thr Asp Gly Pro Cys Lys Ile Pro Val Gln Met Ala Val Asp Met Gln
        35                  40                  45

Thr Leu Thr Pro Val Gly Arg Leu Ile Thr Ala Asn Pro Val Ile Thr
    50                  55                  60

Glu Ser Thr Glu Asn Ser Lys Met Met Leu Glu Leu Asp Pro Pro Phe
65                  70                  75                  80

Gly Asp Ser Tyr Ile Val Ile Gly Val Gly Asp Lys Lys Ile Thr His
                85                  90                  95

His Trp His Arg Ser Gly
            100

<210> SEQ ID NO 9
<211> LENGTH: 1542
<212> TYPE: DNA

```
<213> ORGANISM: Marburg virus
<220> FEATURE:
<221> NAME/KEY: misc_feature
<222> LOCATION: (772)..(773)
<223> OTHER INFORMATION: deletion of mucin-like domain

<400> SEQUENCE: 9
atgaagacta catgtctctt tatcggtctt atcttgatcc aaaggataaa aactcttcct      60
attttagaga tagctagtaa caaccaaccc caaaatatgg attcggtatg ctccggaact     120
ctccagaaga cagaagatgt ccatctgatg ggattcacac tgagtgggca aaaagttgct     180
gattcccctt tggaggcatc caagcgatgg gctttcagga caggtgtacc tcccaagaat     240
gttgagtata cagaagggga ggaagccaaa acatgctaca atataagtgt aacggatccc     300
tctggaaaat ccttgctgtt ggatcctcct accaacatcc gtgactatcc taaatgcaaa     360
actatccatc atattcaagg tcaaaaccct catgcgcaag ggatcgccct ccatctgtgg     420
ggagcatttt tcctgtatga tcgcattgcc tccacaacaa tgtaccgagg cagagtcttc     480
actgaaggga acatagcagc tatgattgtc aataagacag tgcacaaaat gattttctcg     540
aggcaaggac aagggtaccg tcacatgaat ctgacttcta ctaataaata ttggacaagt     600
aacaacggaa cacaaacgaa tgacactgga tgcttcggcg ctcttcaaga atacaactcc     660
acgaagaatc aaacatgtgc tccgtccaaa ataccttcac cactgcccac aacccgctca     720
gagattaaac ccacaagcac cccaactgat gccaccgcac tcaacaccac acaacatctt     780
gtatatttca gaaagaaacg aagtatcctc tggagggaag gcgacatgtt ccctttttctg     840 gacgggttaa taaatgctcc aattgatttt gatccagttc caaatacaaa gacgatcttt     900
gatgaatctt ctagttctgg tgcttcggct gaggaagatc aacatgcctc ccccaatatc     960
agtttaactt tatcctattt tcctaatata atgaaaaca ctgcctactc tggagaaaat    1020
gagaacgatt gtgatgcaga gttaagaatt tggagcgttc aggaggatga cctggcagca    1080
gggctcagtt ggataccgtt ttttggcccct ggaatcgaag actttatac tgctggttta    1140 attaaaaacc aaaacaattt ggtctgcagg ttgaggcgtc tagccaatca aactgccaaa    1200
tccttggaac tcttattaag agtcacaacc gaggagagga cattttcctt aattaataga    1260
catgccattg attttctact cacaaggtgg ggaggaacat gcaaagtgct tggacctgat    1320
tgttgcatcg gaatagaaga cttgtccagg aatatttcag agcaaattga ccaaatcaaa    1380
aaagatgaac aaaaagaggg gactggttgg ggtctaggtg gtaaatggtg gacatccgac    1440
tggggtgttc ttactaactt gggcattttg ctactattat ccatagctgt cttgattgct    1500
ctatcctgta tttgtcgtat ctttaccaaa tatatcgggt aa                       1542
```